United States Patent [19]
Anderson et al.

[11] Patent Number: 5,786,160
[45] Date of Patent: Jul. 28, 1998

[54] NATURAL KILLER CELL-SPECIFIC ANTIGEN AND ANTIBODIES THAT IDENTIFY THE SAME

[75] Inventors: Paul Anderson, Belmont, Mass.; Eric Vivier, Marseilles, France

[73] Assignee: Dana-Farber Cancer Institute, Boston, Mass.

[21] Appl. No.: 484,748

[22] Filed: Jun. 7, 1995

Related U.S. Application Data

[63] Continuation-in-part of Ser. No. 113,170, filed as PCT/US94/09714, Aug. 26, 1994, abandoned.

[51] Int. Cl.$^6$ .............. A61K 33/395; C07K 16/28; G01N 33/579

[52] U.S. Cl. .............. 435/7.24; 424/140.1; 424/153.1; 424/183.1; 435/7.9; 435/325; 435/329; 435/343.1; 436/518; 436/548; 530/387.3; 530/387.5; 530/388.73; 530/391.1; 530/391.3; 530/391.7

[58] Field of Search ................. 435/7.24, 7.9, 435/240.27, 343.1, 329, 325; 436/518, 548; 530/387.3, 387.5, 388.7, 391.1, 391.3, 391.7, 388.73; 424/140.1, 153.1, 173.1, 183.1

[56] References Cited

U.S. PATENT DOCUMENTS

| | | | |
|---|---|---|---|
| 4,772,552 | 9/1988 | Hercend et al. | 435/7 |
| 4,797,475 | 1/1989 | Terasaki et al. | 530/387 |
| 4,831,122 | 5/1989 | Buchsbaum et al. | 530/389 |
| 5,068,223 | 11/1991 | Lipsky et al. | 514/19 |
| 5,169,939 | 12/1992 | Gefter et al. | 530/387.3 |
| 5,215,927 | 6/1993 | Berenson et al. | 436/541 |

OTHER PUBLICATIONS

Baume et al., "Differential Responses to Interleukin 2 Define Functionally Distinct Subsets of Human Natural Killer Cell, "*Eur. J. Immunol.*, 22:1–6 (1992).
Caterson et al., "Identification of a Monoclonal Antibody That Specifically Recognizes Corneal and Skeletal Keratan Sulfate, "*J. Biol. Chem.*, 258(14):8848–8854 (1983).
Chou et al., "Structure of Sulfated Glucuronyl Glycolipids in the Nervous System Reacting with HNK-1 Antiboby and Some IgM Paraproteins in Neuropathy, "*J. Biol. Chem.*, 261(25):11717–11725 (1986).
*Antibodies: A Laboratory Manual*, Harlow, D. L., Ed., Cold Spring Harbor Laboratory, Cold Spring Harbor, New York, 1988, pp. 321–323 and pp. 626–629.
Lanier, et al., "The Relationship of CD16 (LEU–11) and LEU–19 (NKH–1) Antigen Expression on Human Peripheral Blood NK Cells and Cytotoxic T Lymphocytes, "*J. Immunol.*, 136(12):4480–4486 (Jun. 15, 1986).
McCoy et al., "Carbohydrates in the Functions of Natural Killer Cells, "*Glycobiology*, 1(4):321–328 (1991).
Moretta et al., "Allorecognition by NK Cells: Nonself or no self ?, "*Immunology Today*, 13(8): 300–305 (1992).

Nagler et al., "Comparative Studies of Human FcRIII-Positive and Negative Natural Killer Cells, "*J. Immunol.*, 143(10): 3183–3191 (Nov. 15, 1989).
Ohmori et al., "Sialyl SSEA-1 Antigen Carbohydrate Marker of Human Natural Killer Cells and Immature Lymphoid Cells, "*Blood*, 74(1):255–261 (1989).
Parkman, R., "The Biology of Bone Marrow Transplantation for Severe Combined Immune Deficiency, "*Advances In Immunology*, (Dixon, F.J., ed.), Academic Press, Inc., New York, vol. 49 p.381–411 (1991).
Perussia et al., "Antibody 3G8, Specific for the Human Neutrophil Fc Receptor, Reacts with Natural Killer Cells,"*J. Immunol.*, 132(3):1410–1415 (Mar. 1984).
Phillips et al., "Ontogeny of Human Natural Killer (NK) Cells: Fetal NK Cells Mediate Cytolytic Function and Express Cytoplasmic CD3e, δProteins."*J. Exp. Med.*, 175:1055–1066 (Apr. 1992).
Ravetch et al., "Alternative Membrane Forms of FcγRIII (CD16) on Human Natural Killer Cells and Neutrophils: Cell Type–Specific Expression of Two Genes That Differ in Single Nucleotide Substitutions,"*J. Exp. Med.*, 170:481–497 (Aug. 1989).
Schubert, et al., "N17 Cluster Report: CD57, "*Leucocyte Typing IV: White Cell Differentiation Antigens*, Oxford University Press, 1989.
Sharon, N., *Complex Carbohydrates, Their Chemistry, Biosynthesis, and Functions*, Addison–Wesley Publishing Company, Inc., Reading, Massachusetts, 1975, pp. 48–64.
Sorrell, et al., "Human Keratinocytes Contain Carbohydrates That Are Recognized by Keratan Sulfate–Specific Monoclonal Antibodies, "*J. Invest. Dermatol.*, 95(3):347–352 (1990).
Stocks et al., Expression of the CD15 Differentiation Antigen (3–fucosyl–N–acetyl–lactosamine, Le$^x$) on Putative Neutrophil Adhesion Molecules CR3 and NCA–160, *Biochem. J.*, 268:275–280 (1990).
Trinhieri, G., "Biology of Natural Killer Cells.", *Advances in Immunology*, vol. 47, 1989, pp. 187–376.
Young et al., "Identification of Ganglio–N–Tetraosylceramide, as a New Cell Surface Marker for Murine Natural Killer (NK) Cells,"*J. Immunol.*, 124(1):199–201 (Jan. 1980).
Yu et al., "Murine Natural Killer Cells and Marrow Graft Rejection, "*Annu. Rev. Immunol.*, 10:189–213 (1992).

(List continued on next page.)

*Primary Examiner*—David Saunders
*Attorney, Agent, or Firm*—Ostrager, Chong & Flaherty

[57] ABSTRACT

A novel natural killer cell-specific molecule, designated as PEN5, consisting essentially of a glycoprotein pair called PEN5α and PEN5β, having apparent molecular weights of 120–150 and 210–245 kdal, respectively. Monoclonal antibodies, including immunoreactive fragments and derivatives thereof, that bind to unique epitopes present on this NK cell-specific molecule; hybridomas that produce the monoclonal antibodies; methods of using the antibodies and fragments and derivatives; and methods for detecting and/or removing natural killer cells from a sample containing a mixed population of cells are also provided.

35 Claims, 15 Drawing Sheets

OTHER PUBLICATIONS

Yokoyama, W.M., "The Ly-49 and NKR-P1 Gene Families Encoding Lectin-Like Receptors on Natural Killer Cells: The NK Gene Complex,"*Annu. Rev. Immunol.*, 11:613-635 (1993).

Coulter Cytometry Catalogue; Monoclonal Antibodies, Reagents, Kits and Instruments, May 1991, pp. 37-38.

Monoclonal Antibody Source Book, Section 4.46, Becton Dickinson Immunocytometry Systems, 2350 Qume Drive, San Jose, CA 95131-1807.

Ferrara et al., "Evidence That Large Granular Lymphocytes of Donor Origin Mediate Acute Graft-Versus-Host Disease, "*Transplantation*, 47(1):50-54 (Jan. 1989).

MacDonald et al., "Prevention of Acute Lethal Graft-Versus-host Disease in $F_1$Hybrid Mice By Pretreatment of the Graft with Anti-NK-1.1 and Complement."*Transplantation*, 54(1):147-151 (Jul. 1992).

Martin et al., "Human Marrow Transplantation: An Immunological Perspective."*Advances In Immunology*, vol. 40, pp. 379-431.

E. Vivier et al., Jour. Exper. Med., 178, 2023-2033, 1993.

E.Vivier et al., Amer. Jour. Pathol., 146, 409-418, 1995.

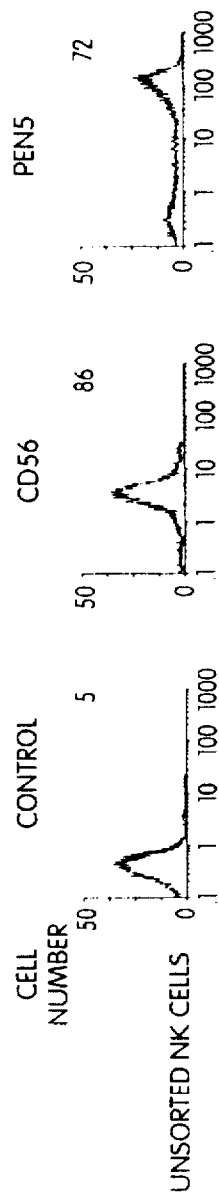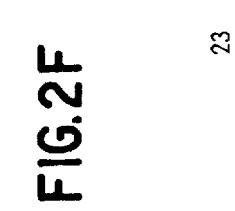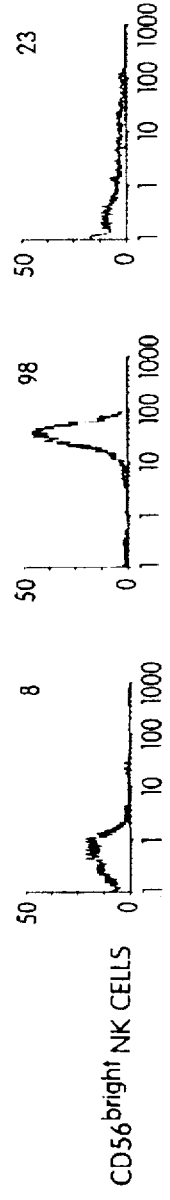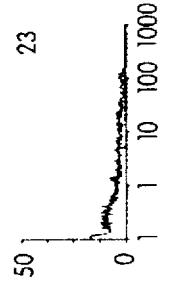

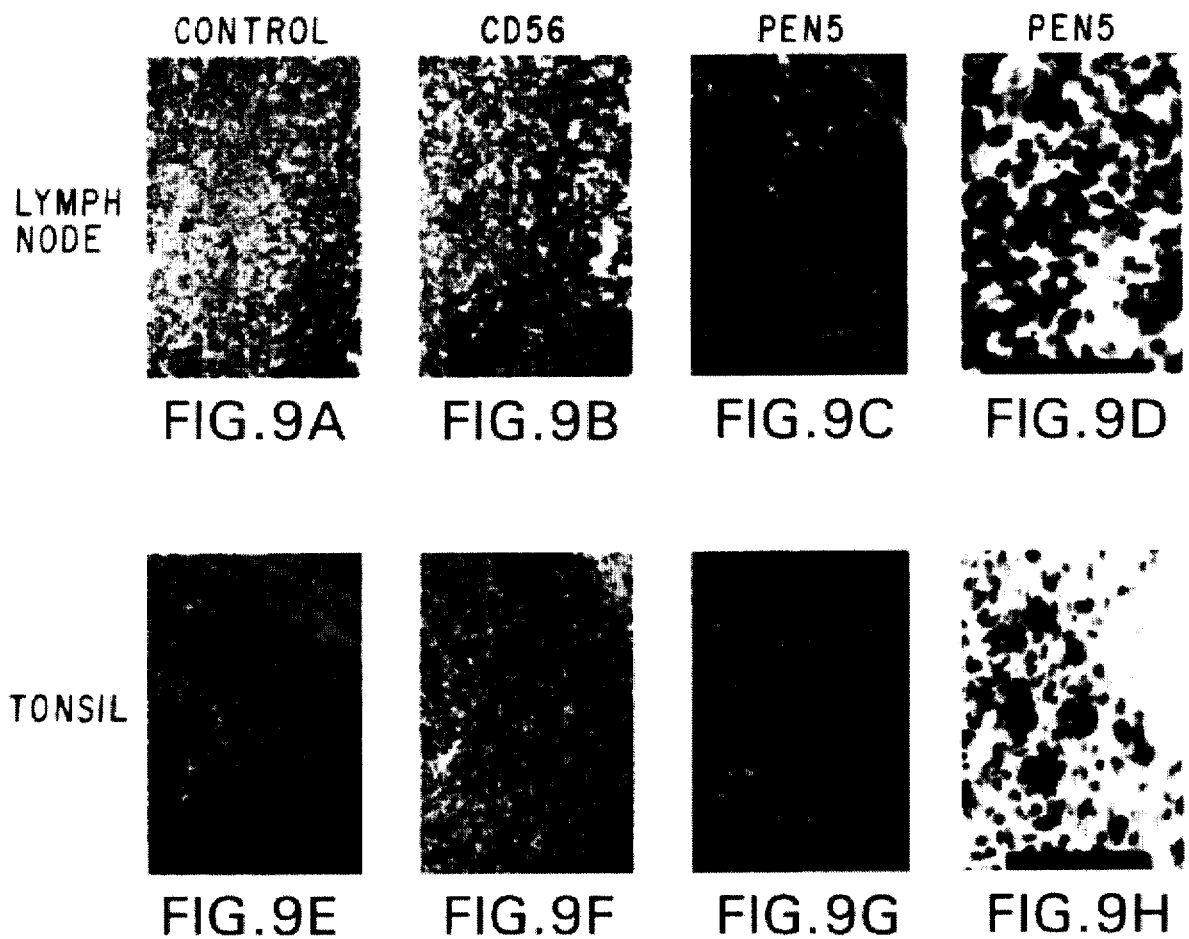

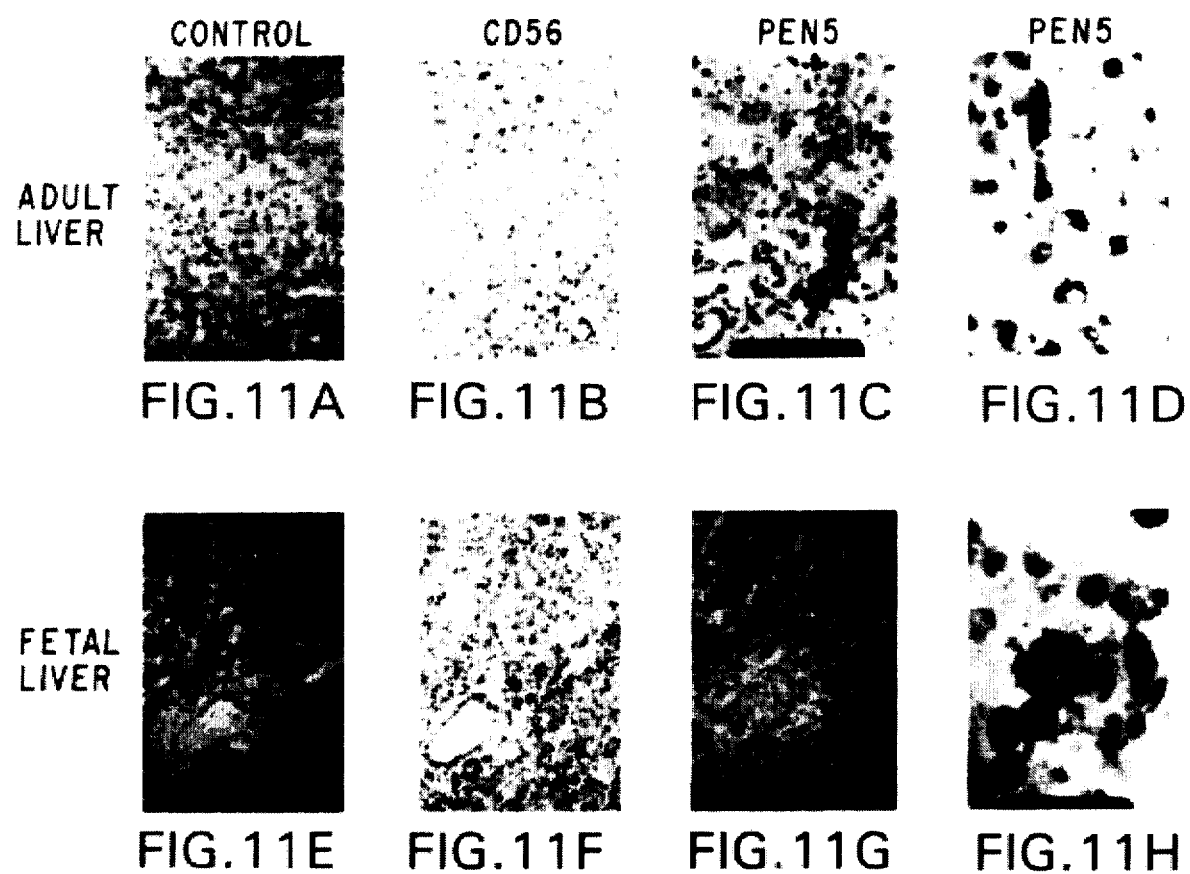

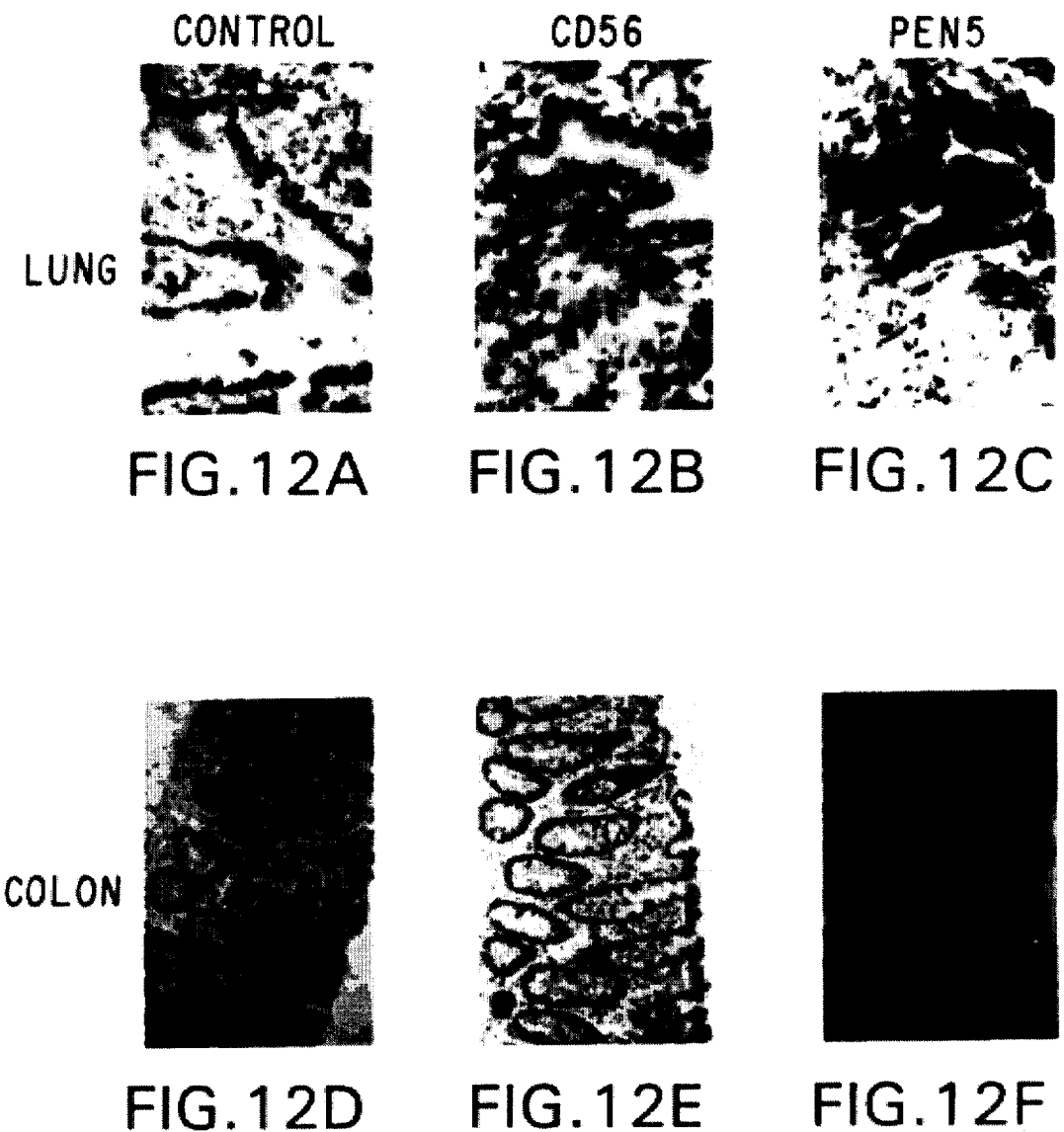

NATURAL KILLER CELL-SPECIFIC ANTIGEN AND ANTIBODIES THAT IDENTIFY THE SAME

CROSS REFERENCE TO RELATED APPLICATION

This application is a continuation of PCT application No. PCT/US94/09714, filed Aug. 26, 1994, which is a continuation-in-part of U.S. application Ser. No. 08/113,170, filed Aug. 27, 1993 and now abandoned.

A STATEMENT OF GOVERNMENT RIGHTS IN INVENTION

This work was supported by a National Institutes of Health grant, CA53595. The government of the United States of America has certain rights to this invention.

FIELD OF THE INVENTION

The invention relates to novel cell surface structures that are selectively expressed on a subpopulation of natural killer cells and to antibodies that bind to unique epitopes on these structures.

BACKGROUND OF THE INVENTION

Natural killer cells (hereinafter sometimes referred to as "NK cells") are large granular lymphocytes ("LGLs") comprising 2–15% of peripheral blood mononuclear cells in healthy individuals. Although NK cells do not rearrange or express either of the known T cell receptor complexes, they can recognize and kill certain virus-infected and transformed cells in a non-MHC-restricted fashion, without prior sensitization. With the exception of CD16, an Fc receptor for immunoglobulin that recognizes antibody-coated target cells, the NK cell surface receptors responsible for target cell recognition have not been identified. The lack of a defining surface receptor requires NK cells to be identified by a combination of phenotypic and functional characteristics.

Although most NK cells are CD3:TCR−, CD16+, CD56+ LGLs, there is considerable phenotypic and functional heterogeneity within this population (Trinchieri, *Adv. Immunol.*, 47:187 (1989)). For example, the surface density of CD56 has been shown to define functionally distinct NK cell populations. $CD56^{bright}$ NK cells are largely $CD16^+$, agranular lymphocytes deficient in cytolytic effector function that proliferate vigorously in response to exogenous IL-2. $CD56^{dim}$ NK cells are $CD16^+$ LGLs possessing potent cytolytic effector function that do not proliferate in response to IL-2. Because some T cells express both CD16 and CD56, these molecules, by themselves, cannot define the NK cell population. (Trinchieri, 1989). Furthermore, because the expression of CD56 on the functionally differentiated population of NK cells is low, monoclonal antibodies reactive with CD56 cannot be used to reliably distinguish this subpopulation of NK cells from other cells in a sample.

It is an object of the present invention to identify a novel cell surface structure that is preferentially expressed on functionally differentiated natural killer cells, which can be used to reliably identify this subpopulation of peripheral blood mononuclear cells.

It is another object of the invention to provide antibodies that will bind to unique epitopes present on a cell surface structure selectively expressed on functionally differentiated NK cells.

SUMMARY OF THE INVENTION

These as well as other objects and advantages are achieved in accordance with the present invention, which provides a partially purified preparation of a novel natural killer cell-specific molecule, to monoclonal antibodies and immunoreactive fragments and derivatives thereof that bind to unique epitopes present on this NK cell-specific molecule, and to hybridomas that produce the monoclonal antibodies. Methods of using the antibodies and fragments and derivatives are also provided.

The novel NK cell-specific molecule of the invention consists essentially of a pair of polydispersed glycoproteins, designated herein as PEN5α and PEN5β, having apparent molecular weights of 120–150 and 210–245 kdal, respectively, as determined by SDS polyacrylamide gel electrophoresis on a 6% polyacrylamide gel under non-reducing conditions. The unique epitopes of the PEN5α/PEN5β glycoprotein pair are preferentially expressed on the subpopulation of peripheral blood NK cells which are of the phenotype $CD16^+$ $CD56^{dim}$ relative to their expression on peripheral blood NK cells having the phenotype $CD16^+$ $CD56^{bright}$ and are not present on $CD3^+$ T lymphocytes or $CD20^+$ B lymphocytes. In preferred embodiments of the invention, the antibody is unreactive with peripheral blood T cells, activated T cells, thymocytes, peripheral blood B cells, splenic B cells, activated B cells, monocytes, granulocytes, platelets, and red blood cells. The antibodies of the invention are preferably monoclonal antibodies and in particularly preferred embodiments, are of mouse or human origin, or they are chimeric antibodies having at least the constant region thereof of human origin.

All monoclonal antibodies having the above specificity and characteristics are encompassed by the present invention. The monoclonal antibodies are produced by hybrid cell lines using conventional hybridization and screening techniques, such as those described in Anderson et al, *J. Immunol.*, 143:1899 (1989), which is hereby incorporated by reference. As is well known in the monoclonal antibody art, independently produced hybrid cell lines that produce monoclonal antibodies specific for a given antigenic determinant are typically distinct from one another, as is each of the monoclonal antibodies so produced. Thus, while repetition of the procedure described herein can result in the production of a hybrid cell line that produces a useful monoclonal antibody in accordance with the invention, it is unlikely that it will produce a hybrid cell line that produces a monoclonal antibody that is chemically an exact copy of the monoclonal antibody described below.

In another embodiment of the invention, the epitope recognized by the antibodies of the invention is a sulfated polylactosamine carbohydrate related to keratan sulfate glycosaminoglycan.

In yet another embodiment, the antibodies have the characteristics of the monoclonal antibody, alternatively referred to herein as either anti-PEN5 or mAb 5H10, secreted by a hybridoma identified by ATCC Accession No. HB11441.

The antibodies and/or immunoreactive fragments or derivatives of the invention can be labeled, e.g. with a radioactive, enzymatic, or fluorescent label and used to detect, enumerate, and/or purify functionally differentiated NK cells in a mixed population of cells and to distinguish these cells from non-NK cells and NK cells that are not functionally differentiated. Identification of the functionally differentiated subpopulation of NK cells involves (a) contacting a suitable sample that contains a mixed population of cells, which can be, for example, peripheral blood, bone marrow aspirate, or lymphoid tissue, with an antibody of the invention or an immunoreactive fragment or derivative thereof, and (b) detecting immune complex formation.

Immune complex formation can be detected by any of the techniques that are conventional and well known in the art.

The antibodies of the invention can also be used to selectively eliminate functionally differentiated NK cells that are of the phenotype CD16$^+$ CD56$^{dim}$ in a sample comprising a mixed population of cells. Thus, in another aspect of the invention, methods are provided for selectively eliminating or removing functionally differentiated natural killer cells from a suitable sample, preferably a biological sample, which involve (a) contacting the sample with an antibody of the invention or an immunoreactive fragment or derivative thereof, which is optionally linked to a radionucleotide or a toxin, and (b) removing from the sample the cells that bind to the antibody, fragment or derivative. In preferred embodiment of the invention, the biological sample is bone marrow aspirate.

These as well as other features and advantages of the present invention will be apparent to persons skilled in the art from the following detailed description and the claims.

BRIEF DESCRIPTION OF THE DRAWINGS

FIGS. 2A–2I comprise three sets of histograms that collectively show the expression of the PEN5 epitope on distinct NK cell subsets. For the experiments that generated these histograms, purified NK cells were either unsorted, or sorted into CD56$^{dim}$ and CD56$^{bright}$ NK cell subsets using rhodamine-conjugated anti-CD56 mAb and flow cytometry. Unsorted NK cells, CD56$^{dim}$ and CD56$^{bright}$ NK cells were further analyzed for the expression of the PEN5 epitope using biotinylated anti-PEN5 mAb and FITC-conjugated avidin. Controls were performed using mouse isotype matched control mAb. The numbers in each histograms indicate the percent of positive stained cells.

In FIG. 7A, I$^{125}$-labeled 5H10 mAb (1×10$^6$ cpm/sample) was preincubated for 20 min at 4° C. in PBS in the presence of the indicated concentrations of bovine cornea keratan sulfate (BC). The mixture was then added to NK cells for another 20 min incubation at 4° C., prior to three washes in PBS-1%BSA. Samples were counted in a γ-counter, and results are expressed as mean cpm of duplicate samples (SD<10%). When used in incubation with NK cells or anti-PEN5 mAb, the following carbohydrates used at 10 mg/ml were without any effect on anti-PEN5 binding to the NK cell surface: chondroitin sulfate B, heparin, heparan sulfate, dextran sulfate, GlCNAc, mannose 6-phosphate, lactose, galactose-6-phosphate, fucose, glucose 6-phospate, glucose and galactose.

In FIG. 7B, peripheral blood NK cells were incubated in PBS-1%BSA for 3 hr with glycosidases (0.025 U/ml) or 45 min with proteases (5 mg/ml) at 37° C., respectively. Cell surface expression of the PEN5 epitope was then analyzed by flow cytometry using anti-PEN5 mAb. Percent modulation was calculated as the ratio of the total linear mean fluorescence intensity of the treated cells over that of untreated control cells.

In FIG. 7C, the antigenicity of anti-PEN5 mAb for aggrecan proteoglycans was analyzed by ELISA as described in the Examples. The anti-keratan sulfate mAb 5D4 was used as a positive control. Chondroitinase ABC was used at 0.04 U/ml, keratanase I was used at 0.05 U/ml and keratanase II was used at 0.004 U/ml, for 1 hr at 37° C. In FIG. 7C, the cross-hatched bars represent reactivity with the anti PEN5 antibody, 5H10, while the open bars represent reactivity with the control antibody, 5D4. Abbreviations used are: CD1=embryonic chick cartilage aggrecan; BNC=bovine nasal cartilage aggrecan; RC=swarm rat chondrosarcoma aggrecan; and SHK=shark cranial cartilage aggrecan.

FIGS. 9A–9H illustrate a comparative histochemical staining of normal adult lymph node and tonsil. Magnification of PEN5 staining shown in FIGS. 9D and 9H is 40×.

Figure 1A:
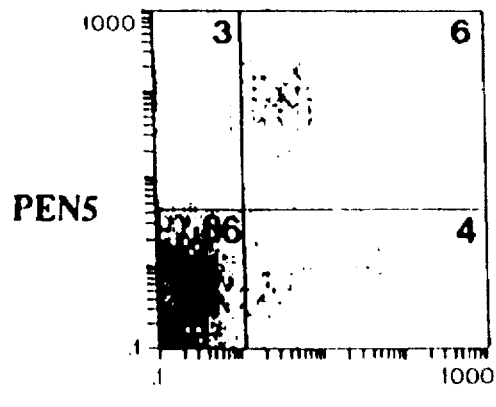
FIGS. 1A–1D comprise four two-color flow cytometry histograms, which collectively show that the PEN5 epitope is expressed selectively on CD56$^+$ CD16$^+$ peripheral blood lymphocytes ("PBL"). PBL were stained by 2-color flow cytometry using rhodamine-conjugated anti-CD56 mAb, rhodamine-conjugated anti-CD3 mAb, rhodamine-conjugated anti-CD20 mAb, FITC-conjugated anti-CD16 mAb or biotinylated anti-PEN5 mAb. The binding of biotinylated anti-PEN5 mAb was revealed using APC-conjugated avidin. Numbers in each quadrants indicate the percent of positive stained cells.
Figure 1B:
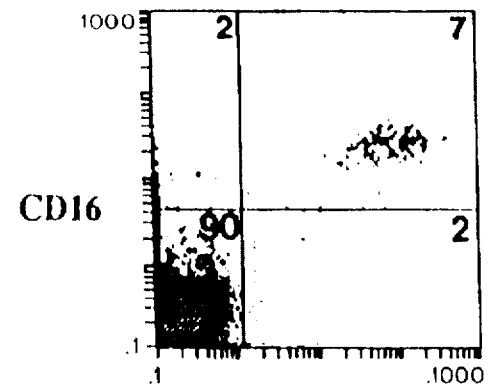
Figure 1C:
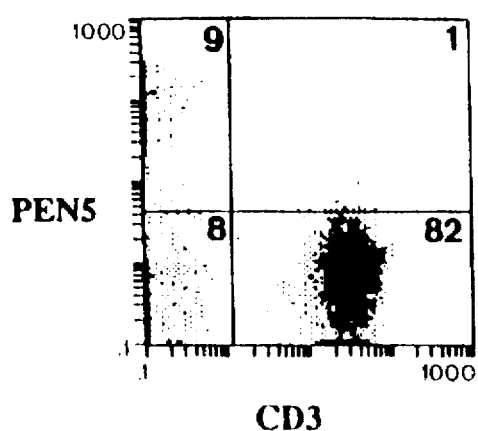
Figure 1D:
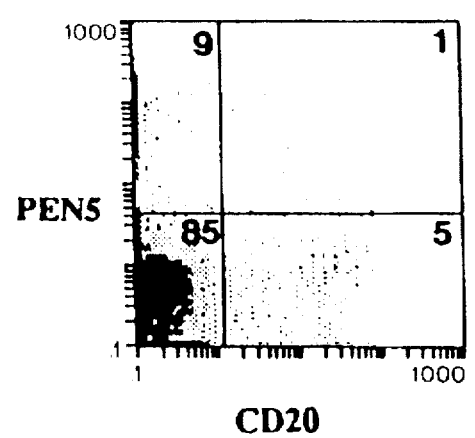

Magnification in all Figures panels is 10×. Monoclonal antibodies used to stain tissue sections, and specific methods are described in the Materials and Methods found at Example 6.

FIGS. 10A–10F illustrate comparative histochemical staining of normal adult and fetal thymus. Magnification of adult thymus stained with control and PEN5 specific antibodies is 20×. Magnification of all other sections is 10×. Monoclonal antibodies used to stain tissue sections, and specific methods are described in the Materials and Methods found at Example 6.

FIGS. 11A–11H illustrate comparative histochemical staining of normal adult and fetal liver. Magnification of adult liver stained with anti-PEN5 is 20× (FIG. 11C) and 40× (FIG. 11D). Magnification of fetal liver stained with PEN5 is 10× (FIG. 11G) and 60× (FIG. 11H). Magnification of all other panels is 10×. Monoclonal antibodies used to stain tissue sections, and specific methods are described in the Materials and Methods found at Example 6.

FIGS. 12A–12F illustrate the comparative histochemical staining of normal adult lung and colon. Magnification of lung stained with anti-CD56 and anti-PEN5 is 20×. Magnification of all other sections is 10×.

FIGS. 13A through 13D illustrate dual labeling of tissue infiltrating lymphocytes. Tissue sections from adult spleen (FIGS. 13A and 13B) or adult appendix (FIGS. 13C and 13D) were double labeled with fluorescein tagged anti-PEN5 (FIGS. 13A and 13C) and rhodamine tagged anti-TIA-1 (FIGS. 13B and 13D), prior to examination by fluorescent microscopy. Black arrowheads show the location of PEN5$^+$ cells in FIGS. 13A and 13C. White arrowheads show the location of both PEN5$^+$ cells and TIA-1$^+$ cells in FIGS. 13B and 13D.

DETAILED DESCRIPTION OF THE INVENTION

Natural killer cells are CD3:TCR$^-$, CD16$^+$, CD56$^+$ large granular lymphocytes. Two functionally distinct populations of peripheral blood NK cells can be differentiated by their surface expression of an isoform of the neural cell adhesion molecule, NCAM (also known as CD56). CD56$^{bright}$ NK cells have the attributes of an undifferentiated cell in that they proliferate vigorously in response to exogenous cytokines, but largely lack cytolytic activity. CD56$^{dim}$ NK cells have the attributes of a more differentiated cell, in that they proliferate poorly in response to exogenous cytokines, but are potent cytolytic effector cells. Several monoclonal antibodies that recognize human CD56 are available commercially, for example from Coulter Corp. (Hialeah, Fla.) and AMAC, Inc. (Westbrook, Me.).

NK cells are capable of mediating two types of cytotoxic effector function: natural cytotoxicity and antibody-dependent cellular cytotoxicity ("ADCC"). In this capacity, NK cells play an important role in host defense against viral infection, and in immune surveillance against the establishment of transformed cells. More recent results indicate that NK cells can effect a primitive form of allorecognition which can contribute to graft rejection during allogeneic transplantation and also to graft-versus-host disease. For these reasons, the reliable identification of NK cells within the mononuclear cell population is of great importance. The present invention relates to the identification and molecular characterization of a novel sulfated polylactosamine epitope whose expression is largely restricted to the functionally differentiated population of LGLs previously characterized as CD16$^+$ CD56$^{dim}$, cytolytic effectors and to antibodies that are capable of recognizing the same. Because this epitope is not expressed on resting or activated T cells, resting or activated B cells, monocytes, granulocytes, platelets or red blood cells, antibodies that bind to unique epitopes on the PEN5 glycoprotein pair can be used to directly identify this important population of mononuclear cells. Furthermore, because the epitope is preferentially expressed on the functionally differentiated subpopulation of NK cells relative to CD56$^{bright}$ NK cells that have the attributes of an undifferentiated cell, antibodies that bind to the epitope can be used to distinguish these two subpopulations of NK cells from one another.

Thus, in one aspect of the invention there is provided an antibody or fragment or derivative thereof, that recognizes a unique epitope of the PEN5 glycoprotein pair. As used herein, the phrase "unique epitope" means any epitope on the PEN5α glycoprotein and/or the PEN5β glycoprotein, which like the novel sulfated polylactosamine epitope identified herein, is present on a high percentage, e.g., at least about 70%, of the population of LGLs previously characterized as CD56$^{dim}$, CD16$^+$ natural killer cells and on a significantly lower percentage of the population of NK cells that are phenotypically CD16$^+$ CD56$^{bright}$, but not on CD3$^+$ T cells, or CD20+ B cells. The "unique epitope" may be present on a glycosylated form of the PEN5 glycoprotein pair as it is ordinarily expressed on the cell surface of CD56$^{dim}$, CD16$^+$ natural killer cells as previously described, or, the "unique epitope" may be present on an unglycosylated or deglycosylated form of the PEN5 glycoprotein pair. As used herein, the term "unglycosylated" means a PEN5molecule where both the PEN5α and the PEN5β glycoproteins are free of any covalently attached carbohydrate moieties. As used herein, the term "deglycosylated" means a PEN5 molecule where either or both of the PEN5α glycoprotein or the PEN5α glycoprotein is partially glycosylated but does not contain the same full contingent of carbohydrate moieties as the PEN5α glycoprotein or the PEN5β glycoprotein as it is ordinarily expressed on the cell surface of CD56$^{dim}$, CD16$^+$ natural killer cells.

The antibodies, fragments, and derivatives of the invention are useful as research reagents, to unambiguously identify, quantify and/or purify natural killer cells in a mixed population of cells and in isolating these natural killer cells therefrom. The antibodies, fragments and derivatives of the invention may also be useful therapeutically, either alone, in combination with complement, or conjugated to a radioactive material or a toxin to treat disorders of the immune system where NK cells are implicated as mediators of disease, especially graft-versus-host disease and solid organ and allogenic bone marrow transplant rejection. Monoclonal antibodies, and chimeric and humanized antibodies, are preferred for detection and therapy, respectively. Antibodies, fragments and derivatives thereof recognizing a unique epitope on a deglycosylated or unglycosylated form of the PEN5 molecule, may be useful in the diagnosis and treatment of immune disorders associated with NK cells expressing PEN5 exhibiting an aberrant glycosylation pattern compared to PEN5 normally expressed on NK cells.

In the following description, reference will be made to various methodologies known to those of skill in the art of immunology, cell biology, and molecular biology. Publications and other materials setting forth such known methodologies to which reference is made are incorporated herein by reference in their entireties as though set forth in full.
Preparation And Research Uses Of Antibodies Monoclonal antibodies of the invention can be prepared using any technique that provides for the production of antibody molecules by continuous cell lines in culture. These include, but are not limited to, the original techniques of Köhler and Milstein, *Nature*, 265:495–497 (1975), modified as described in Anderson et al, *J. Immunol.*, 143:1899 (1989), the pertinent portions of which are hereby incorporated by reference and the more recent human B cell hybridoma technique and EBV-hybridoma technique well known to persons skilled in the art.

As part of the production of the monoclonal antibodies of the invention, various host animals, including but not limited to rabbits, mice, hamsters, and rats can be immunized by injection with NK cells that express the PEN5 glycoprotein and, after a sufficient time, the animal is sacrificed and spleen or other immune cells obtained. The preferred immunogen to be used in the immunization protocol is a preparation of freshly isolated NK cells, purified from peripheral blood lymphocytes by negative selection. Other immunogens that alternatively could be used include partially purified preparations of the PEN5 molecule, the PEN5α glycoprotein or the PEN5β glycoprotein, including the glycosylated, deglycosylated or unglycosylated forms thereof and derivatives and fragments thereof. A partially purified preparation of the PEN5 molecule can be prepared from permeabilized NK cells following immunoprecipitation and SDS gel electrophoresis using 6% polyacrylamide gel as hereinafter described using techniques well known to persons skilled in the art. However, any suitable method for partially purifying the PEN5 molecule or the PEN5α or the PEN5β glycoprotein as described above can be satisfactorily employed and alternative methods of partial purification will be readily apparent to those persons skilled in this area of technology. Once the protein core(s) of the PEN5α and PEN5β molecules have been cloned, recombinantly produced molecules can also be used as an immunogen. The spleen or other immune cells obtained from the animal are immortalized by fusing the spleen cells with an immortalized cell line, generally in the presence of a fusion enhancing reagent, for example, polyethylene glycol. The resulting cells, which include the fused hybridomas, are then allowed to grow in a selective medium, such as HAT medium, and the surviving cells are grown in such medium using limiting dilution conditions. The cells are grown in a suitable container, e.g., microtiter wells, and the supernatant is screened for monoclonal antibodies having the desired specificity.

In a preferred embodiment, the monoclonal antibodies of the present invention are prepared as described in the Examples.

Screening procedures that can be used to screen hybridoma cells producing antibodies to a PEN5 epitope include, but are not limited to, (1) enzyme-linked immunoadsorbent assays (ELISA), (2) immunoprecipitation and (3) fluorescent activated cell sorting (FACS) analyses. Many different ELISAS that can be used to screen for anti-PEN5 monoclonal antibodies can be envisioned by persons skilled in the art. These include but are not limited to formats comprising purified or recombinantly produced PEN5 glycoproteins attached to a solid phase or formats comprising the use of freshly isolated whole NK cells or cell lysate membrane preparations either attached to the solid phase or bound to antibodies attached to the solid phase. Samples of hybridoma supernatants would be reacted with either of these two formats, followed by incubation with, for instance, goat-anti-mouse immunoglobulin complexed to an enzymesubstrate that can be visually identified.

Initial screening is preferably conducted by screening hybridoma supernatants by flow cytometry for their reactivity with NK cells, but not with T cells, B cells, and monocytes. Further characterization of the hybridomas for those that produce monoclonal antibodies that are preferentially expressed on NK cells that are phenotypically $CD16^+ CD56^{dim}$ relative to NK cells that are phenotypically $CD16^+ CD56^{bright}$ can be conducted by testing on purified populations of lymphoid and non-lymphoid cells by indirect immunofluorescence assays and flow cytometry, substantially as described in the Examples herein. Monoclonal antibodies that recognize a PEN5 epitope that is preferentially expressed on functionally differentiated NK cells will react with an epitope that is present on a high percentage NK cells that phenotypically are $CD56^{dim} CD16^+$ cells, e.g., at least about 70–90%, preferably about 80%, of such cells, and with a much lower percentage of NK cells that are phenotypically $CD16^+ CD56^{bright}$ (e.g., about 10 to 35%), but will not react with $CD3^+$ T cells or $CD20^+$ B cells. In preferred embodiments, the antibody will also be unreactive with monocytes, granulocytes, platelets, and red blood cells. Monoclonal antibodies that compete with the 5H10 antibody in competition assays well known to persons skilled in the art are likely to recognize essentially the same epitope as mAb 5H10, while monoclonal antibodies that fail to compete with mAb 5H10 but nevertheless meet the criteria of being unique to the $CD16^+$, $CD56^{dim}$ subpopulation of NK cells are likely to recognize a different epitope on the PEN5 glycoprotein pair. Both classes of antibodies are considered within the scope of the present invention.

Once the desired hybridoma has been selected and cloned, the resultant antibody may be produced in one of two major ways. The purest monoclonal antibody is produced by in vitro culturing of the desired hybridoma in a suitable medium for a suitable length of time, followed by the recovery of the desired antibody from the supernatant. The length of time and medium are known or can readily be determined. This in vitro technique produces essentially monospecific monoclonal antibody, essentially free from other species of anti-human immunoglobulin. However, the in vitro method may not produce a sufficient quantity or concentration of antibody for some purposes, since the quantity of antibody generated is only about 50 μg/ml.

To produce a much larger quantity of monoclonal antibody, the desired hybridoma may be injected into an animal, such as a mouse. Preferably the mice are syngeneic or semi-syngeneic to the strain from which the monoclonal-antibody producing hybridomas were obtained. Injection of the hybridoma causes formation of antibody producing tumors after a suitable incubation time, which will result in a high concentration of the desired antibody (about 5–20 mg/ml) in the ascites of the host animal.

Antibody molecules can be purified by known techniques, e.g. by immunoabsorption or immunoaffinity chromatography, chromatographic methods such as high performance liquid chromatography or a combination thereof.

Following these protocols, any person skilled in this area of technology can readily isolate hybridomas that produce monoclonal antibodies exhibiting specificity for a unique epitope on functionally differentiated natural killer cells. Although only a single hybridoma producing a monoclonal antibody (5H10) against the human PEN5 epitope is exemplified by way of working example, it is contemplated that the present invention encompasses all monoclonal antibodies exhibiting the characteristics of mAb 5H10 as herein described.

For example, it was determined that the subject monoclonal antibody 5H10 belongs to the class IgM. However, a monoclonal antibody exhibiting the characteristic described herein may be of class IgG, subclass $IgG_1$, $IgG_2\alpha$, $IgG_2\beta$, or $IgG_3$, or of classes IgM, IgA, or other known Ig classes. The differences among these classes or subclasses will not affect the selectivity of the reaction pattern of the antibody, but may affect the further reaction of the antibody with other materials, such as (for example) complement or anti-mouse antibodies. Although the subject antibody is specifically IgM, it is contemplated that antibodies having the patterns of reactivity illustrated herein are included within the subject invention regardless of the immunoglobulin class or subclass to which they belong.

Moreover, while the specific example of the novel antibody of the present invention is from a murine source, this is not meant to be a limitation. The above antibody and those antibodies having the characteristics of the mAb 5H10, whether from a mouse source, other mammalian source including human, rat, or other sources, or combinations thereof, are included within the scope of this invention, as set forth above.

The antibodies may be used for the detection and enumeration by indirect staining of $CD16^+$, $CD56^{dim}$ subpopulation of NK cells in normal individuals or in disease states, for example by fluorescence microscopy, flow cytometry, immunoperoxidase, or other indirect methodoloples. Panning techniques are also possible. The antibodies may also be used for purification of human natural killer cells which are $CD16^+$, $CD56^{dim}$.

Preparation of Fragments and Derivatives of Antibodies

Also included within the scope of the present invention are antibody fragments and derivatives which comprise at least the functional portion of the antigen binding domain of an anti-PEN5antibody molecule.

Antibody fragments which contain the binding domain of the molecule can be generated by known techniques. For example, such fragments include, but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent. See, e.g., National Institutes of Health, 1 *Current Protocols In Immunology*, Coligan et al., ed. §§ 2.8, 2.10 (Wiley Interscience, 1991).

Antibody fragments also include Fv fragments, i.e., antibody products in which there are no constant region amino acid residues. Such fragments can be produced, for example as described in WO 92/04381 or U.S. Pat. No. 4,642,334.

When antibodies produced in non-human subjects are used therapeutically in humans, they are recognized to varying degrees as foreign and an immune response may be generated in the patient. One approach minimizing or eliminating this problem, which is preferable to general immmunosuppression, is to produce chimeric antibody derivatives, i.e. antibody molecules that combine a nonhuman animal variable region and a human constant region. Chimeric antibody molecules can include, for example, the antigen binding domain from an antibody of a mouse, rat, or other species, with human constant regions. A variety of approaches for making chimeric antibodies have been described and can be used to make chimeric antibodies containing the immunoglobulin variable region which recognize a unique epitope on the PEN5 antigen. See, for example, Morrison et al., *Proc. Natl. Acad. Sci. U.S.A.* 81:6851 (1985); Takeda et al., *Nature* 314:452 (1985), Cabilly et al., U.S. Pat. No. 4,816,567; Boss et al. U.S. Pat. No. 4,816,397; Tanaguchi et al., Eur. Patent Pub. EP171496; Eur. Patent Pub. 0173494; United Kingdom Patent GB 2177096B. Such chimeras produce a less marked immune response than non-chimeric antibodies.

For human therapeutic purposes, the monoclonal or chimeric antibodies of the invention can be further humanized by producing human constant region chimeras, in which even parts of the variable regions, especially the conserved or framework regions of the antigen-binding domain, are of human origin and only the hypervariable regions are of non-human origin. Such altered immunoglobulin molecules may be made by any of several techniques known in the art, (e.g., Teng et al., *Proc. Natl. Acad. Sci. U.S.A.*, 80:7308–7312 (1983); Kozbor et al., *Immunology Today*, 4:7279 (1983); Olsson et al., *Meth. Enzymol.*, 92:3–16 (1982)), and are preferably made according to the teachings of PCT Pub. WO 92/06193 or EP 0239400. There are also a number of companies that humanize antibodies commercially, for example Scotgen Limited, 2 Holly Road, Twickenham, Middlesex, Great Britain.

These humanized antibodies are preferable for immunotherapy in that they minimize the effects of an immune response. This in turn leads to a lowering of any concomitant immunosuppression and to include increased long term effectiveness in, for instance, chronic disease situations or situations requiring repeated antibody treatments.

Antibody Conjugates For Detection and Therapy

In addition to molecular antibody fragments and derivatives, antibody derivatives or immmnoconjugates consisting of an antibody molecule or binding region thereof bound to a label such as a radioisotope, fluorescent tag (e.g., fluorescein isothiocyanate, phycoerythrin, phycoerythrin Cy5, or rhodamine), enzyme (e.g., biotin), or other tracer molecule can be made by techniques known in the art. Alternatively, the antibody molecule or fragment thereof can be bound to a therapeutically useful biological or chemical molecule targeted to its desired site of action by virtue of the antibody's binding specificity. As one example of such an embodiment, a cytotoxic compound can be conjugated to an antibody of the invention which is specific for NK cells which are the causative agents of an immune disorder, for example, bone marrow graft rejection. The cytotoxic compound, which can be for example, a radionucleotide or a toxin, such as diphtheria toxin, in conjugated form is thus targeted to the implicated NK cells.

Immunoassays

The antibodies of the invention and the fragments and derivatives thereof containing the binding region (e.g., Fab, Fab', $F(ab')_2$), can be used in various immunoassays. Such immunoassays include, but are not limited to, competitive and non-competitive assay systems using techniques such as radioimmunoassays, ELISA (enzyme linked immunosorbent assay), "sandwich" immunoassays, precipitin reactions, gel diffusion precipitin reactions, immunodiffusion assays, agglutination assays, complement fixation assays, immunoradiometric assays, fluorescent immunoassays, protein A immunoassays, and immunoelectrophoresis assays, to name but a few.

Differentiated NK cells, especially human NK cells, can be detected in a biological sample including a mixed population of cells, for example, hematopoietic and lymphoid cells, using the antibodies, fragments or derivatives. Suitable biological samples include peripheral blood, bone marrow aspirate and lymphoid tissue. When used in an assay as described, the antibody is typically labeled so that its binding with the relevant NK cell subpopulation can be detected. Any suitable label well known to persons skilled in the art, including but not limited to fluorescent dyes, radioactive isotopes, enzymes which catalyze a reaction producing detectable products, biotin, or metal ions detectable by nuclear magnetic resonance can be employed.

Therapeutic Applications of NK Cell-Specific Antibodies, Fragments and Derivatives Bone marrow transplantation is increasingly used for the treatment of disorders of the immune system, aplastic anemia, and especially hematopoietic malignancies, such as acute lymphocytic leukemia. For many years, graft-versus-host disease ("GVHD") and its attendant complications have presented a serious problem in human bone marrow transplantation. When it became apparent that T cells contained within the bone marrow inoculum are effectors of GVHD, many bone marrow transplant programs resorted to using T-cell depleted bone marrow cells. This procedure has somewhat successfully reduced the incidence and severity of GVHD. However, several new problems have emerged as a result of T cell depletion, including an increased incidence of bone marrow graft rejection. Furthermore, GVHD continues to be a serious problem in many bone marrow transplantation recipients, especially in non-T cell depleted transplants.

Several lines of evidence have directly implicated natural killer cells in graft rejection, and more recently, in graft-versus-host disease. For example, treatment of recipients with an antiserum specific for NK cells (Lotzova et al, *Transplantation*, 35:490 (1983)) ablated allograft resistance and injection of recipients with NK clones caused allograft rejection in UK cell deficient beige mice which do not manifest marrow graft rejection. Warner et al., *Nature* 300:31 (1982). See also, Martin et al, *Advances Immunol.*, 40:379–431 (1987), Yu et al *Amer. Rev. Immunol.*, 10:189–213 (1992) and Moretta et al, *Immunol. Today*, 13:300–305 (1992).

The scientific literature also suggests that NK cells may play a deleterious role in graft-versus-host disease ("GVHD") following solid organ or tissue transplants. (Ferrara et al, *Transplantation*, 47:50–54 (January, 1989); MacDonald and Gartner, *Transplantation*, 54:147–151 (July, 1992)). See also, U.S. Pat. No. 4,772,552.

Since the antibodies of the invention can be used to target the functionally differentiated subpopulation of NK cells specifically, the invention may also be useful prophylactically and therapeutically, in the prevention and treatment of graft rejection in solid organ and bone marrow transplantation, and in graft-versus-host disease, by modulating the function and number of cytolytic effector NK cells in vivo. Although it is contemplated that the anti-NK cell-specific antibodies and fragments and derivatives thereof will have applicability for animal subjects in addition to human beings, such as domesticated animals, the therapeutic aspects of the invention are of the greatest value in the treatment of disorders in humans.

For example, in bone marrow transplantation, the antibodies, fragments and derivatives of the invention can be used to remove the CD16⁺ CD56$^{dim}$ cytolytic effector population of cells from bone marrow aspirates ex vivo, prior to transplantation of the marrow into the marrow recipient. Removal of these natural killer cells from the bone marrow aspirate can be accomplished by conventional methods, such as those used in immunological T cell depletion. Antibodies that exhibit the ability to lyse NK cells in the presence of complement can be used in combination with complement to treat the bone marrow ex vivo prior to transplantation, to kill the NK cells that might otherwise contribute to the etiology of graft-versus-host disease in the recipient. Alternatively, the anti-PEN5 antibody might be linked to a toxin as described, to kill the cytolytic effector NK cells. The antibodies, fragments or derivatives of the invention could also be administered to the bone marrow recipient in vivo prior to the transplantation procedure.

The selective in vivo removal of NK cells may also prove useful in the treatment of autoimmune diseases such as SLE, which are in part mediated by NK cells.

The antibodies, fragments, or derivatives of the invention may also be useful in the prophylaxis and/or treatment of solid organ graft rejection and bone marrow rejection, especially in allogeneic bone marrow transplant recipients where T cell depletion has been employed.

When used prophylactically or therapeutically in vivo, the NK-specific antibodies, fragments or derivatives of the invention may be useful in unmodified form for modulating the number and function of the cytolytic effector population of NK cells, or they can be conjugated to radionucleotides or toxins by means well known in the art and used to deliver the conjugated substance to deleterious NK cells for negative modulation. Non-limiting examples of radionucleotides which can be conjugated to antibodies and administered include $^{212}$Bi, $^{131}$I, $^{186}$Re, and $^{90}$Y. These elements exert their effect by locally irradiating the cells, leading to various intracellular lesions, well known to persons skilled in the art of radiotherapy.

Cytotoxic drugs that can be conjugated to antibodies and administered for in vivo therapy include, but are not limited to, daunorubicin, doxorubicin, methotrexate, and mytomycin C. For a more detailed discussion of these classes of drugs and their mechanisms of action, see, Goodman et al., *Goodman and Gilman's The Pharmaceutical Basis Of Therapeutics*, 8th ed. Pergamon Press (1991).

As an example of conjugation to a toxin, an anti-PEN5 monoclonal antibody can be combined with diphtheria toxin, by the method of Bumol, *Proc. Natl. Acad. Sci.*, 80:529 (1983). Briefly, monoclonal antibodies reactive with an NK cell specific epitope are prepared as described by Bumol. The antibodies are purified and combined with excess (6 mol/mol) N-succinimydyl 3-(2-pyridyldithio) propionate (Pharmacia, Uppsala, Sweden) in PBS. After 30 minutes incubation at room temperature, the solution is dialyzed against PBS. The modified antibodies are conjugated with an appropriate toxin, such as diphtheria toxin A chain. Other toxins such as ricin A can also be employed. The diphtheria toxin A chain is isolated as detailed in Bumol, supra. The modified antibodies are mixed with excess (3 mol/mol) reduced diphtheria toxin A chain (10% of the total volume), allowed to react for 36 hours at 4° C., and concentrated by chromatography on Sephadex G-2000. The product is applied to a Sephadex G200 column (1.0×100 cm), allowed to equilibrate and eluted with PBS.

Using these and other similar techniques known to persons in the art, the effector population of natural killer cells can be selectively eliminated in the transplant recipient.

The route of administration for the in vivo therapeutic modalities may include intradermal, intramuscular, intraperitoneal, intravenous, or subcutaneous injection, intranasal routes and slow release forms, such as those delivered in transplantable forms, on patches or in other colloidal forms. In one embodiment, the antibody can be encapsulated in liposomes.

The effective dose of the therapeutic reagent will be a function of the particular reagent employed, the presence and nature of conjugated therapeutic reagent, the patient, and his or her clinical condition. Effective doses of the antibodies, fragments, or derivatives of the invention for use in preventing, suppressing, or treating an immune-related disease are in the range of about 1 ng to 100 mg/kg body weight. A preferred dosage range is between about 10 ng and 10 mg/kg, and a more preferred dosage range is between 100 ng and 1 mg/kg.

Various pharmacologic compositions may be utilized in order to deliver the antibodies, or fragments or derivatives thereof, according to the invention. Any suitable pharmaceutical agent with desirable solubility characteristics and chemical properties may be used, including but not limited to, where appropriate, saline or dextrose solutions. The reagent itself must be properly formulated, for example, as a humanized or chimeric antibody combined with various buffers, sugars, or stabilizing compounds that increase the stability or half life of the antibody. To extend the half-life, the reagent can first be modified to increase or decrease the amount of carbohydrate complexed to it, or alternatively, can be complexed with a reagent such as polyethylene glycol. Finally, pharmaceutical compositions comprising the therapeutic reagent in the appropriate buffers, salts, and pH are required.

Therapeutic kits can comprise the therapeutic compositions of the invention in one or more containers.

The PEN5α/PEN5β Glycoprotein Pair

The invention also provides partially purified preparations of the NK cell-specific molecule, called PEN5α/PEN5β, that is preferentially expressed on the subpopulation of NK cells previously characterized as CD16$^+$, CD56$^{dim}$ NK cells. The molecule consists essentially of two membrane bound glycoproteins.

As used herein, use of the term "partially purified preparation" with respect to the PEN5 means the PEN5 molecule, consisting essentially of the PEN5α and PEN5β glycoprotein pair as herein described, which has been purified from permeabilized NK cells following immunoprecipitation and SDS gel electrophoresis using 6% polyacrylamide gel as hereinafter described. After the glycoproteins are fractionated on a gel, they can be recovered and renatured in accordance with known and established techniques.

As expected of a marker of functional differentiation, expression of the PEN5 epitope is down-modulated by stimuli which induce NK cell proliferation, and is largely absent from the leukemic NK cells of patients with granular lymphocyte proliferative disorder.

Immunoprecipitations of freshly isolated human NK cell detergent lysates with mAb 5H10 revealed that the molecule consists essentially of two distinct glycoproteins and also revealed that the average molecular weight of the larger species, PEN5α, is 227±4 kDa (n=12). The molecular weight range of the polydispersed PEN5α species was 210±3 kDa to 245±5 kDa. The average molecular weight of the smaller species, PEN5β, was 140±3 kDa, with a range of 123±3 kDa to 170±4 kDa. The migration of both PEN5α and PEN5β as polydispersed bands suggests that both species are highly glycosylated.

Enzymatic deglycosylation indicates that both PEN5α and PEN5β are 80–90% carbohydrate by weight. This result raised the possibility that these proteins are either proteoglycans or mucin-type glycoproteins.

Proteoglycans are high molecular weight glycoproteins in which specific glycosaminoglycans are bound to proteins via Gal-xylose-Ser linkages [Bhavanandan, *Glycobiolocy*, (1991)], or in the case of keratan sulfate chains, terminal galactosamine linkages to serine or threonine. The studies described in the Examples below reveal that PEN5 molecules are free of xylose-linked carbohydrates. However, the anti-PEN5 mAbs are reactive with sulfated polylactosamine carbohydrates present on keratan sulfate glycosaminoglycans, which raised the possibility that PEN5α and/or PEN5β glycoproteins may be cell surface-associated keratan sulfate proteoglycans.

Two types of keratan sulfate proteoglycans have been described: cartilage-type keratan sulfate proteoglycans are O-linked glycoproteins, whereas cornea-type keratan sulfate proteoglycans are N-linked glycoproteins. Since PEN5α is an N-linked glycoprotein, it is possible that PEN5α is an unusual cell surface cornea-type keratan sulfate proteoglycan. Similarly, PEN5β is an O-linked glycoprotein sensitive to keratanase treatment, and may be a cartilage-type keratan sulfate proteoglycan. However, the inability of six distinct anti-keratan sulfate mAbs to bind to NK cells, coupled with the lack of detection of S$^{35}$sulfur-labeled material in 5H10 (anti-PEN5) immunoprecipitates prepared from S$^{35}$ sulfur metabolically-labeled NK cells, indicate that the PEN5 glycoproteins are not keratan sulfate proteoglycans.

Alternatively, it has been reported that mucin-type glycoproteins secreted by cultured hamster tracheal epithelial cells are sensitive to keratanase I treatment and contain polylactosamine carbohydrates [Wu, *Biochem J.*, 277:713 (1991)]. Mucin-type glycoproteins are highly glycosylated proteins containing a majority of O-linked oligosaccharides, and are associated with the cell membrane in a number of cell types [Carraway, *Glycobiology* 1:131 (1991); Strous, *Rev. Biochem Mol. Bio.* 27:57 (1992); Devine, 35 (1992). Classification of PEN5β as an NK cell specific membrane-bound mucin-type glycoprotein is most consistent with our data. By contrast, the high content of N-linked carbohydrates in PEN5α is not consistent with its classification as a mucin-type glycoprotein. Therefore the PEN5α:PEN5β complex appears to be analogous to the ASGP-1:ASGP-2 complex derived from ascitic mammary adenocarcinoma cells [Sherblom, *J. Biol. Chem.*, 225:12051 (1980) in which only one component (ASGP-1) of the complex is a mucin-type glycoprotein. The developmentally regulated PEN5βmucin-like glycoprotein, like other cell surface mucins, may contribute to cytoprotection during lymphocyte mediated cytolysis.

The biochemical features of PEN5 molecules points the way for future research. First, carbohydrates are major mediators of cell-cell interactions [Jessel, *Annu. Rev. NeuroSci.*, 13:227 (1990)]. In particular, ligands for E- and P-selectins have been shown to contain either sialyl-CD15 or CD57 polylactosamine epitopes [Philips, *Science*, 250:1130 (1990); Larsen, *Cell*, 63:467 (1990); Needham, *PNAS*, 90:927 (1993)], and GlyCAM-1 a membrane bound mucin glycoprotein is the ligand for L-selectin [Lasky, 1992 #1853]. The NK cell surface expression of the sulfated polylactosamine PEN5 epitope, as well the mucin-like biochemical characteristics of PEN5β, raise the possibility that PEN5 glycoproteins contribute to NK cell specific adhesion. Second, in their protease-resistance as well as their extended rod-like structure, the PEN5 glycoproteins resemble epithelial cell mucins. The mucin-type glycoproteins serve a protective role on the epithelial cell surface, and have been shown to protect cells from attack by cytotoxic lymphocytes. The PEN5 glycoproteins may therefore protect NK cells from their own cytolytic machinery. The selective expression of PEN5 proteins on the terminally differentiated subset of NK cells would be consistent with their acquisition of fully competent cytotoxic function. Exogenous mucins have been shown to inhibit NK cell killing, supporting their potential involvement in resistance to NK cell cytolytic functions [ogata, *Cancer Res.*, 52:4741 (1992)].

The PEN5 antigen can be used in preparing and/or purifying the antibodies of the invention and should also be useful in identifying the natural counter-receptor for the PEN5 antigen on target cells. Amino acid sequence information obtained from the PEN5 glycoprotein pair can also be used to clone the PEN5β and PEN5β glycoprotein chains in accordance with established techniques.

Deposit Information

Samples of the hybridoma (designated herein as 5H10) that secretes anti-NK cell-specific mouse monoclonal mAb 5H10 were deposited with the American Type Culture Collection, ATCC 12301 Parklawn Drive, Rockville, Md. on Aug. 19, 1993 under the terms of the Budapest Treaty and assigned ATCC accession number HB11441. Without admitting that access to the hybrid cell line is necessary to practice the claimed invention, Applicants represent that the ATCC is a depository affording permanence of the deposit and ready accessibility thereto by the public if a patent is granted. All restrictions on the availability to the public of the material so deposited will be irrevocably removed upon the granting of a patent. The material will be available during the pendency of the patent application to one determined by the Commissioner to be entitled thereto under 37 CFR 1.14 and 35 USC 122. The deposited material will be maintained with all the care necessary to keep it viable and uncontaminated for a period of at least five years after the most recent request for the furnishing of a sample of the deposited microorganism, and in any case, for a period of at least thirty (30) years after the date of deposit or for the enforceable life of the patent, whichever period is longer. Applicants and their assignee acknowledges their duty to replace the deposit should the depository be unable to furnish a sample when requested due to the condition of the deposit.

The invention will be more fully understood from the following Examples.

EXAMPLES

Abbreviations

The following abbreviations are used throughout the Examples reproduced below: BCK: bovine cornea keratan sulfate; BNC: bovine nasal cartilage aggrecan; CD1: embryonic chick cartilage aggrecan; LCM: leucocyte-conditioned medium; GLPD: granular lymphocyte proliferative disorder; RC: Swarm rat chondrosarcoma aggrecan; SHK: shark cranial cartilage aggrecan.

Materials and Methods

The following methods and materials apply to Examples 1-5.

Reagents

Peptide-N-glycosidase (PNgase F) and Endo-a-N-acetylgalactosaminidase (O-glycanase) were used in the buffer provided by the manufacturer (Oxford Glycosystems). Keratanase I (keratan sulfate 1,4 b-D-galactanohydrolase; ICN Biomedicals, (Costa Mesa, Calif.), keratanase II which attacks oversulfated forms of (keratan sulfate 1,4 b-D-galactanohydrolase; ICN Biomedicals, (Costa Mesa, Calif.), keratanase II which attacks oversulfated forms of keratan sulfate resistant to keratanase I (Seikagaku America, Rockville, Md.) and neuraminidase (Calbiochem) were used in either PBS, PNgase F or O-glycanase buffers. Chondroitinase ABC (ICN Biomedicals,) was used in sodium acetate 0.05M pH 7.4. Bovine cornea keratan sulfate (BC), as well as other glycosaminoglycans and carbohydrates were purchased from Sigma, (St. Louis, Mo.)., Trypsin, chymotrypsin and pronase E were also obtained from Sigma. FITC- and PE-conjugated avidin were obtained from Becton-Dickinson, (Paramus, N.J.).

Antibodies

Mouse monoclonal antibodies (mAb) reactive with CD2 (T11.1, IgG1), CD3 (RW24B6, IgG2b), CD56 (N901, IgG1), CD20 (B1, IgG1) were obtained from Coulter Corp., as well as isotype matched control mouse ZmAb (IgG and IgM). Radioiodination of PEN5 mAb was performed using Iodobeads (Pierce) as previously described [Vivier, *J. Immunol.* 132:1410 (1991)]. The characterization of the anti-CD16 mAb (3G8, IgG1), and the anti-keratan sulfate mAb 5D4 (IgM) was reported elsewhere [Perussia, *J. Immunol.*, 134:1410 (1984), Caterson, *J. Biol. Chem.*, 258:8848 (1983)]. The following mAb recognize distinct epitopes on most keratan sulfate chains: 1B4 (IgG), 2D3 (IgG), 3D2 (IgM), 4D1 (IgM) and 8C2 [Sorrell, *J. Invest. Dermatol.* 95:347 (1990)]. FITC-labeled goat anti-mouse Ig(G+M) was purchased from Tago.

Cells

All cells were cultured in final medium consisting of RPHI 1640 (Whittaker Bioproducts, (Walkersville, Md.) supplemented with 10% fetal calf serum, 1 mM sodium pyruvate, 2 mM glutamine and 50 mg/ml gentamicin, all obtained from Gibco, (Grand Island, N.Y.) Purified NK cells and T cells were isolated from peripheral blood mononuclear cells (PBMC) obtained from healthy volunteers by negative selection using immuno-magnetic bead depletion [Vivier, *Int. Immunol.*, 4:1313–1323 (1992)]. In some experiments, NK cells and NK cell subsets ($CD56^{bright}$ and $CD56^{dim}$) were further purified by flow cytometric sorting on an Epics V flow cytometer (Coulter Electronics) after staining with anti-CD56 mAb. Activation of NK cells was performed using ionomycin (1 µM) and 20% lymphocyte-conditioned medium (LCM) as described previously [Robertson, *J. Immunol.*, 150:1705 (1993)]. PBMC from three patients with a $CD3:TCR^-$, $CD16^+$, $CD56^+$ granular lymphocyte proliferative disorder (GLPD) [Oshimi, *Leukemia*, 2:617 (1988)] were isolated by Ficoll-Hypaque gradient centrifugation.

Immunoprecipitations

Cells were resuspended in PBS and subjected to radioiodination using $^{125}I$ by the lactoperoxidase method [Vivier, 1991 #1031]. After three washes in PBS, cells were solubilized in NP-40 lysis buffer (1% NP-40, 150 mM NaCl, 50 mM Tris HCl, pH 8.0, 1 mM PMSF, 10 µg/ml leupeptin, 10 µg/ml aprotinin, 10 µg/ml AEBSF) for 15 min on ice. After removing insoluble material by centrifugation at 12.000 rpm for 15 min, radioiodinated lysates were diluted in 1 ml lysis buffer and precleaned three times with 3 µl of affinity-purified rabbit anti-mouse IgM or IgG (RAM, Jackson Immunoresearch Laboratories, (West Grove, Pa.) and 50 ml of a 50% solution of protein A-sepharose beads (Pharmacia, Milwaukee, Wis.). The immunoprecipitations were performed using 3 ml of the indicated mAb, 3 µl of RAM and 50 µl of protein A-Sepharose beads at 50%. Sepharose-bound immune complexes were washed four times in lysis buffer, and eluted either directly into sample buffer (2% SDS, 10% glycerol, 0.1M Tris-HCl, pH 6.8, 0.02% bromophenol blue) prior to electrophoretic separation, or in elution buffer (0.15M $NK_4OH$, pH 10.5) prior to deglycosylation experiments.

Deglycosylation of radioiodinated PEN5

Radioiodinated PEN5 samples eluted from 5H10-coated Sepharose beads, were dried under vacuum and resuspended in appropriate deglycosylation enzyme buffers. The following enzymes were used alone or in combination: PNgase F (310 U/ml), O-glycanase (0.06 U/ml), keratanase I (0.25 U/ml) and neuraminidase (0.2 U/ml).

ELISA for acgrecan-type proteogylcans

Wells of microtiter plates were incubated with 10 µg/ml solutions of the indicated aggrecan-type proteoglycans overnight at 4° C. After washing, wells were incubated with 0.1M Tris, pH 7.6 containing 1% BSA or with the indicated enzymes in this buffer. Following enzymatic digestion, a standard ELISA was performed using 1/1000 dilution of 5H10 (anti-PEN5) and 5D4 (anti-keratan sulfate), and 1/500 dilution of anti-mouse Ig(G+M) conjugated with alkaline phosphatase. Color was developed using p-nitrophenyl phosphate substrate in 0.86M diethanolamine, pH 9.8. All absorbance values are the mean of 4 wells (SD<10%) and have been corrected for non-specific binding of the second antibody.

Transmission electron microscopy

Peripheral blood NK cells were first stained using 5H10 (anti-PEN5) and colloidal gold-labeled goat anti-mouse IgM (Amersham). After fixation using % glutaraldehyde, the stained cells were examined by transmission electron microscopy.

Example 1
Preparation And Characterization Of anti-PEN5 Antibody

In order to identify novel cell surface structures selectively expressed on NK cells, we generated a panel of mouse mAb (anti-PEN mAb) that recognized NK cells but not T cells. These antibodies were produced by immunizing BALB/c mice with digitonin permeabilized peripheral blood NK cells as previously described [Anderson, *J. Immunol.* 143:1889 (1989)]. Briefly, mononuclear cells were isolated from leukopheresis residues (obtained from normal blood donors at the Dana-Farber Cancer Institute Blood Bank) by centrifugation over ficoll. These cells were cultured in plastic flasks in RPMI media containing 10% fetal calf serum for six to twelve hours to allow the adherence of monocytes. Nonadherent cells were incubated with monoclonal antibodies reactive with CD5 (24T6G12, IgG2A), CD3 (RW24B6, IgG1), CD20 (B1H299, IGG2A), CD24 (MY4322A-1, IgG2B) at optimal concentrations for thirty minutes, then washed extensively. Following the addition of magnetic beads coupled to goat anti-mouse Ig (Advanced Magnetics, Inc., Cambridge, Ma.) these populations were depleted of T cells, B cells, monocytes by negative selection using a magnet. The remaining cells which were enriched for NK cells were phenotypically less than 5% $CD3^+$, 75-95% $CD56^+$, and 65-80% $CD16^+$ as determined by flow cytometry using an Epics profile (Coulter Electronics, Hialeah, Fla.). These cells were then permeabilized with digitonin as described in Anderson, *J. Immunol.* 143:1889 (1989). Permeabilized NK cells ($50 \times 10^6$ cells per ml PBS), were injected into a five week old Balb/c mouse at three week intervals for a total of four immunizations. Three days after the last immunization, the immunized mouse was sacrificed and splenocytes prepared using standard methods. Immune splenocytes were fused to the NS1 hybridoma cell line at a 1:1 ratio using polyethylene glycol as described in Anderson, *J. Immunol.* 143:1889 (1989). Following fusion, cells were cultured at limiting dilution in a 96-well plate in the presence of RPMI media containing 10% fetal calf serum and HAT selection medium. Individual supernatants were screened for their reactivity with permeabilized and unpermeabilized NK cells, T cells, B cells, monocytes. Monoclonal antibody 5H10 (anti-PEN5) was selected as an antibody which reacted specifically with peripheral blood NK cells.

More specifically, the reactivity pattern of 5H10 was first determined by testing purified peripheral blood lymphocytes obtained from healthy volunteers using an Epics V flow cytometer (Coulter Electronics, Hialeah, Fla.). Peripheral blood lymphocytes ("PBLs") purified as described in the Methods and Materials, were stained by 2-color flow cytometry using rhodamine-conjugated anti-CD56 mAb, rhodamine-conjugated anti-CD3 mAb, rhodamine-conjugated anti-CD20 mAb, FITC-conjugated anti-CD16 mAb or biotinylated anti-PEN5 mAb in accordance with well established techniques. The binding of biotinylated anti-PEN5 mAb was revealed using APC-conjugated avidin.

The results of the two color flow cytometry are shown in FIG. 1, in which the numbers in each quadrants indicate the percent of positive stained cells.

As shown in FIG. 1, the analysis of PBLs revealed a unique epitope, PEN5, to be expressed on the majority of $CD56^+$ (FIG. 1A) and $CD16^+$ (FIG. 1B) PBLs. In contrast, PEN5 was not significantly expressed on $CD3^+$ T cells (FIG. 1C) or on $CD20^+$ B cells (FIG. 1D).

To test cell surface expression of activated T cells and activated B cells, peripheral blood T cells isolated as described were activated with optimal mitogenic concentrations of PHA and Con A. Splenic B cells were activated with optimal concentrations of *Staphylococcus aureas* Cowan strain I in accordance with standard laboratory protocols. Immunofluorescence staining was performed at days 2, 4, and 6 after activation. Neither T cell activation induced by mitogenic concentrations of PHA or Con A (in the presence or absence of PMA), nor B cell activation induced by *Staphylococcus aureus* Cowan strain I, for 1 to 6 days induced the cell surface expression of the PEN5 epitope (See Table 1 below). Similarly, allogeneic T cell clones ($CD3^+$ $CD4^+$ or $CD3^+CD8^+$) did not express the PEN5 epitope (See Table 2).

Cell surface expression of the antigen recognized by the antibody 5H10 on hematopoietic cells was also assessed by indirect immunofluorescence and flow cytometry in accordance with established protocols. As summarized in Table 1 below, cell surface staining of monocytes, granulocytes, platelets and erythrocytes also failed to reveal the PEN5 epitope, confirming that PEN5 is an NK cell restricted molecule.

TABLE 1

Cell surface expression of PEN5 on hematopoietic cells.

| Cell type | Relative Expression* |
|---|---|
| Peripheral blood T cells | − |
| Activated T cells‡ | − |
| Thymocytes | − |
| Peripheral blood NK cells | ++ |
| NK cell lines: | |
| YT.N17 | − |
| 3.3 | ± |
| NKL | − |
| Peripheral blood B cells | − |
| Splenic B cells | − |
| Activated B cells§ | − |
| Monocytes | − |
| Granulocytes | − |
| Platelets | − |
| Red blood cells | − |

*The cell surface expression of 5H10 was assessed by indirect immunofluorescence and flow cytometry; −: <5% positive stained cells; ±: between 5 and 20% positive stained cells; ++: > 60% positive stained cells.
‡Peripheral blood T cells were activated with optimal mitogenic concentrations of PHA and CON A, and immunofluorescence staining was performed at days 2, 4 and 6 after activation.
§Splenic B cells were activated with optimal mitogenic concentrations of *Staphyllococcus aureus* Cowan strain I, and immunofluorescence staining was performed at days 2, 4 and 6 after activation.

TABLE 2

Absence of surface expression of PEN5 on cytotoxic T cell clones

| | Cell surface expression* | | | | | |
|---|---|---|---|---|---|---|
| Clone | CD3 | CD2 | CD4 | CD8 | CD56 | PEN5 |
| T4C1 | + | + | + | − | − | − |
| 6.5 B4 | + | + | + | − | − | − |

TABLE 2-continued

Absence of surface expression of PEN5 on cytotoxic T cell clones

| Clone | Cell surface expression* | | | | | |
|---|---|---|---|---|---|---|
| | CD3 | CD2 | CD4 | CD8 | CD56 | PEN5 |
| 6.5 C1 | + | + | + | – | – | – |
| 20.1 A2 | + | + | + | – | – | – |
| 8.17 A | + | + | + | – | + | – |
| 20.1 D8 | + | + | – | + | – | – |
| T4T8C1 | + | + | + | – | + | – |

*The cell surface phenotype of the indicated T cell clones was performed by immunofluorescence and flow cytometry. –: 5% positive stained cells; +: >60% positive stained cells.

To more precisely analyze the expression of PEN5 on NK cells, flow cytometric analysis of PEN5 expression was performed on freshly isolated peripheral blood NK cells purified by negative selection using immunomagnetic bead depletion (see Materials and Methods). PEN5 was brightly expressed on 71.7±3.5% (mean±SEM, n=16) of these NK cell preparations whose average phenotype was 75.6±3.3% $CD56^+$, 4.2±4.0% $CD16^+$ and 8.3±3.5% $CD3^+$.

The phenotypic heterogeneity of peripheral blood NK cells required a more careful comparison of the relative expression of PEN5 and CD56. The two-color flow cytometric comparison shown in FIG. 1 suggested that PEN5 was preferentially expressed on the $CD56^{dim}$ population. This was confirmed by comparing the expression of PEN5 on sorted populations of CD56dim and CD56 bright NK cells, as shown in FIG. 2.

Briefly, purified NK cells were sorted into $CD56^{dim}$ and $CD56^{bright}$ NK cell subsets using rhodamine-conjugated anti-CD56 mAb and flow cytometry. Unsorted NK cells, $CD56^{dim}$ and $CD56^{bright}$ NK cells were further analyzed for the expression of 5H10 using biotinylated anti-PEN5 mAb and FITC-conjugated avidin. Controls were performed using mouse isotype matched control IgM mAb. The results of this experiment are illustrated in FIG. 2, in which the numbers in each histogram indicate the percentage of positively stained cells. As shown in FIG. 2, PEN5 was expressed at a high density on 85.9 ±2.2% of $CD56^{dim}$ NK cells (n=4), and at low density on 31.1±5.3% of $CD56^{bright}$ NK cells. These results indicate that high density cell surface expression of the PEN5 epitope is restricted to the functionally differentiated $CD56^{dim}$ NK cells. These results also indicate that the cell surface expression of PEN5 defines two distinct subsets of NK cells, $PEN5^+$ and $PEN5^{dim/-}$ which overlap with the $CD56^{dim}$ and $CD56^{bright}$ NK cell subsets, respectively.

Example 2
PEN5 expression is down-regulated by NK cell activation $CD56^{dim}$ and $CD56^{bright}$ NK cells strongly differ in their response to proliferative stimuli. Although $CD56^{dim}$ NK cells do not proliferate in response to either IL-2 or the combination of ionomycin and PMA, $CD56^{bright}$ NK cells proliferate in response to either stimulus. We took advantage of the recent observation that $CD56^{dim}$ NK cells can be induced to proliferate in response to a combination of LCM and ionomycin to correlate PEN5 expression with the NK cell proliferative state. Briefly, sorted $CD56^{dim}$ and $CD56^{bright}$ NK cells were activated for 20 days with ionomycin and LCM as described in the Materials and Methods. At 0, 6, 8, 10, 14, and 20 days of culture, aliquots of the activated NK cell populations were analyzed for their cell surface phenotype by flow cytometry using isotype matched control mAb, anti-CD56 and 5H10 mAb. The results illustrated in FIG. 3 indicate the percent of positively stained cells (%); the total mean fluorescence intensity is indicated below in the histograms.

Figure 3:
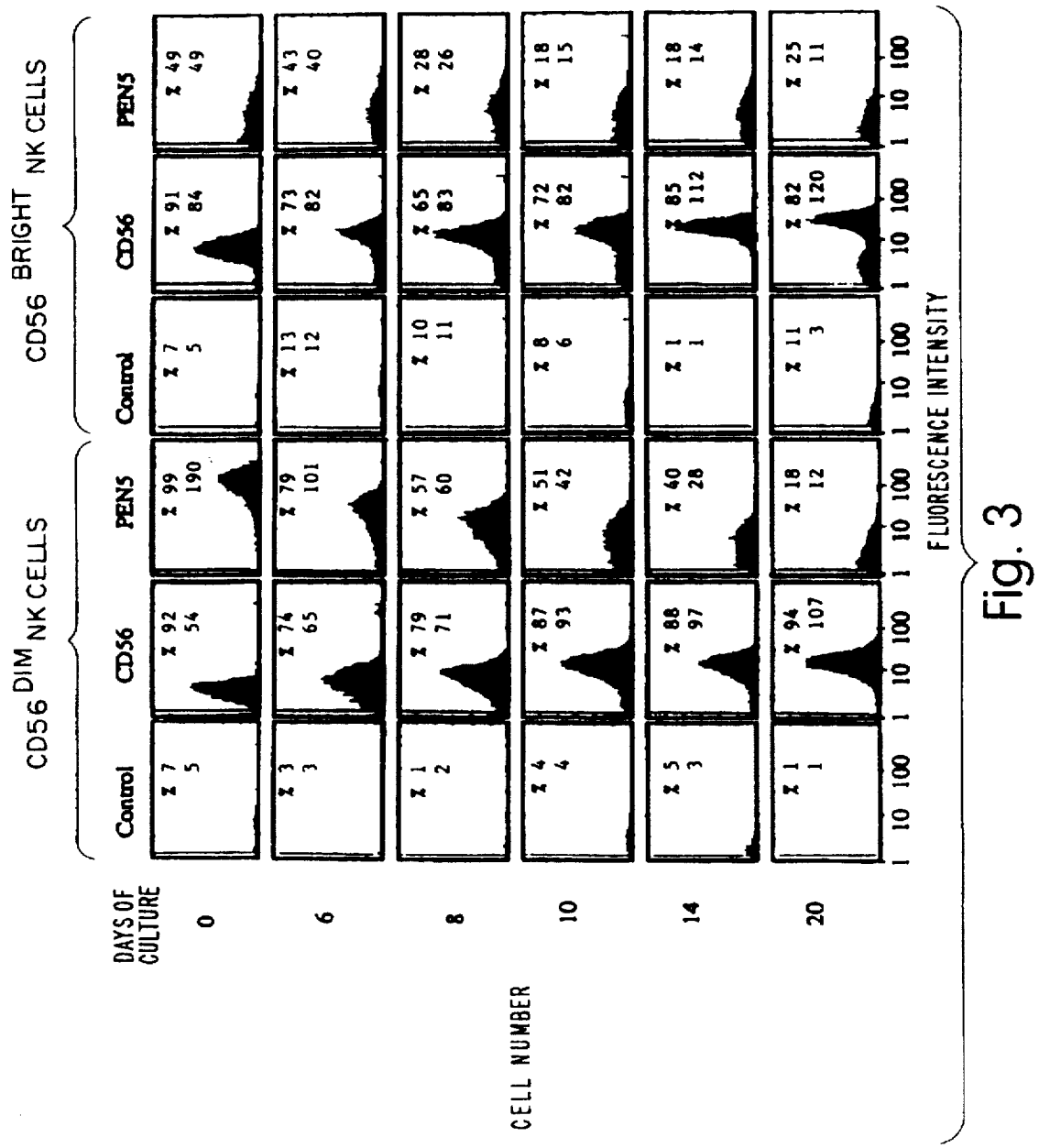
FIG. 3 comprises a series of flow cytometry histograms illustrating the kinetics of PEN5 expression on activated NK cells. Sorted CD56$^{dim}$ and CD56$^{bright}$ NK cells were activated for 20 days with ionomycin and lymphocyte conditioned medium as described in the examples. At the indicated period of time, (i.e. 0, 6, 8, 10, 14, and 20 days of culture) aliquots of the activated NK cell populations were analyzed for their cell surface phenotype by flow cytometry using isotype matched control mAb, anti-CD56 and anti-PEN5 mAb. Results indicate the percent of positively stained cells (%); the total mean fluorescence intensity is indicated below.
Figure 4:
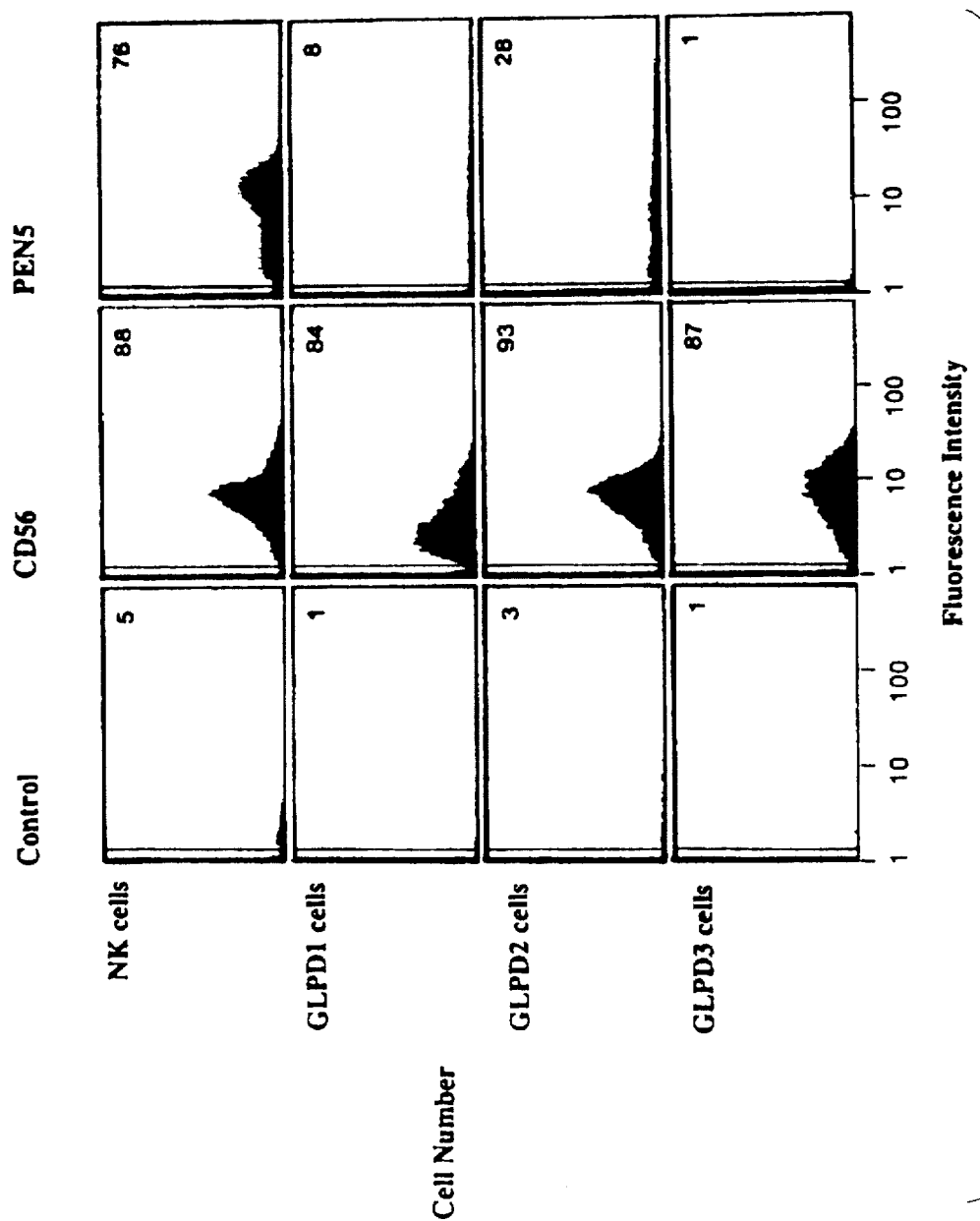
FIG. 4 is a series of flow cytometry histograms that illustrate the cell surface expression of the PEN5 epitope on leukemic NK cells. Peripheral blood NK cells, as well as peripheral blood mononuclear cells (PBMC) isolated from three patients undergoing granular lymphocyte proliferative disorder "GLPD" blast crisis (GLPD1–3) were analyzed for the cell surface expression of CD56 and PEN5 using indirect immunofluorescence and flow cytometry. The numbers in each histogram indicate the percent of positive stained cells.

As shown in FIG. 3, activation of $CD56^{dim}$ NK cells resulted in the temporal reduction of PEN5 expression. In parallel, the cell surface expression of CD56 was temporally increased, and after 20 days of activation, the cell surface expression of PEN5 and CD56 on the $CD56^{dim}$ NK cells was similar to that of unactivated $CD56^{bright}$ NK cells (i.e: $PEN5^{dim/-}$ and $CD56^{bright}$). These results are consistent with the absences PEN5 from the cell surface of long term human NK cell clones (A. Moretta, personal communication). In addition, PEN5 was not expressed on leukemic NK cells ($CD3:TCR^-$, $CD16^+$, $CD56^+$) isolated from patients with granular lymphocyte proliferative disorder (See, FIG. 4). Finally, 5H10 was absent or dimly expressed on three long term human NK cell lines, 3.3, NKL and YT.N17. These results indicate that PEN5 expression inversely correlates with the NK cell proliferative capacity.

Figure 5:
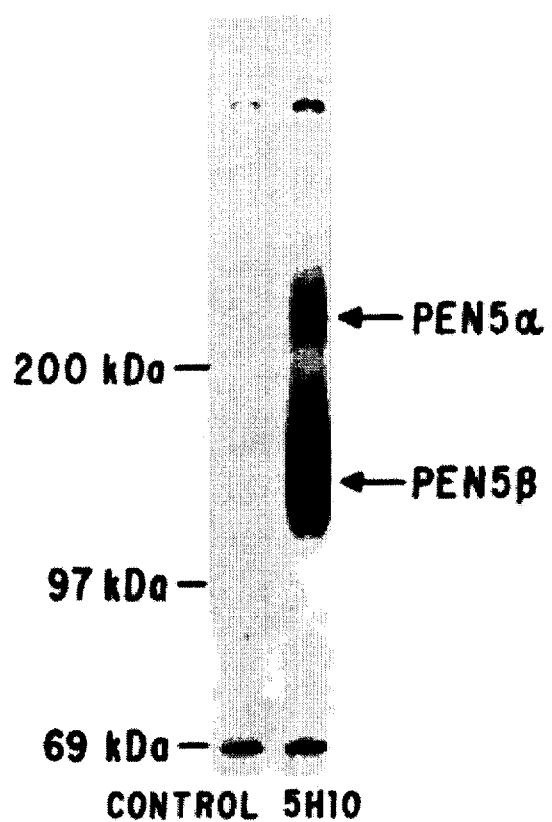
FIG. 5 is a reproduction of an SDS gel from an immunoprecipitation of PEN5 glycoproteins. Detergent lysates prepared from radioiodinated NK cells were immunoprecipitated using 5H10 mAb or mouse IgM control. Samples were then separated under non-reducing conditions on a 6% SDS-polyacrylamide gel.

Example 3
Biochemical characterization of the PEN5 epitope
5H10 Immunoprecipitates Two Polydispersed Bands Radioiodinated lysates prepared from resting NK cells were immunoprecipitated using the 5H10 (anti-PEN5) mAb or an isotype matched mouse IgM control mAb. Immunoprecipitates were then separated under non-reducing conditions on SDS-polyacrylamide gels (6% SDS). The results are shown in FIG. 5.

As illustrated in Figures, two diffuse bands were selectively immunoprecipitated by the 5H10 mAb. The average molecular weight (m.w.) of the larger species, PEN5α, was 227±4 kDa (n=12). The m.w. range of the polydispersed PEN5 species was 210±3 kDa to 245±5 kDa. The average m.w. of the smaller species, PEN5β was 140±3 kDa, with a range of 123±3 kDa to 170±4 kDa. The migration of both PEN5α and β molecules as polydispersed bands suggested that they were highly glycosylated.

PEN5α and β Are Carbohydrates With Keratanase I-Sensitive Chains

Figure 6:
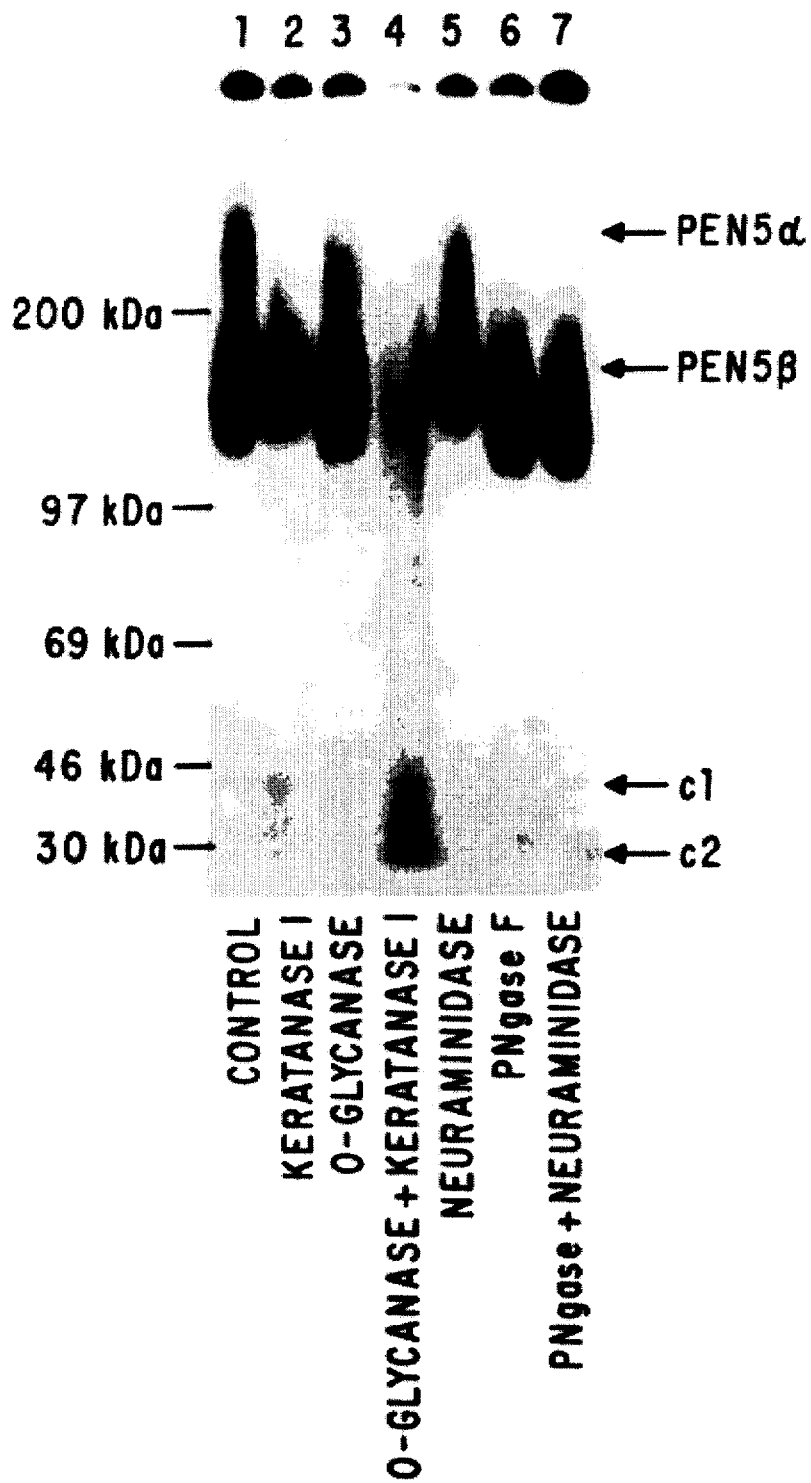
FIG. 6 is a reproduction of an SDS gel from immunoprecipitations performed after enzymatic deglycosylation of PEN5 glycoproteins. Detergent lysates prepared from radioiodinated NK cells were immunoprecipitated using 5H10 mAb. Affinity-purified PEN5α and PEN5β glycoproteins were eluted from the antibody-coated sepharose beads using 0.15M NH$_4$OH, pH 10.5. Aliquots of this dried sample were then subjected to deglycosylation for 24 hr at 37° C. using PNgase F (lane 6), O-glycanase (lane 3), keratanase I (lane 2), O-glycanase and keratanase (lane 4), neuraminidase (lane 6), and PNgase F and neuraminidase (lane 7). Control eluates incubated in phosphate buffered saline (PBS) without any enzymes were separated in lane 1. Samples were separated under non-reducing conditions on a 6–12% SDS-polyacrylamide gradient gel.

These results were confirmed in deglycosylation experiments, the results of which are shown in FIG. 6. In these experiments, detergent lysates prepared from radioiodinated NK cells were immunoprecipitated using 5H10 mAb. Affinity-purified PEN5α and β glycoproteins were eluted from the antibody-coated sepharose beads using 0.15M NH₄OH, pH 10.5. Aliquots of this dried sample were then subjected to deglycosylation for 24 hr at 37° C. using PNgase F (lane 6), O-glycanase (lane 3), keratanase I (lane 2), O-glycanase and keratanase (lane 4), neuraminidase (lane 6), and PNgase F and neuraminidase (lane 7). Control eluates incubated in PBS without any enzymes were separated in lane 1. Samples were separated under non-reducing conditions on a 6–12% SDS-polyacrylamide gradient gel.

Compared to the migration of untreated PEN5 glycoproteins (FIG. 6, lane 1), PNgase F treatment induced the disappearance of PEN5α from the 210–245 kDa m.w. range, and the appearance of a deglycosylated form of PEN5a migrating at 20–25 kDa (c2). In contrast, the apparent mobility of PEN5β was reduced by only ~20 kDa after PNgase F incubation. Treatment of PEN5 glycoproteins with O-glycanase (FIG. 6, lane 3) did not significantly affect their SDS-PAGE migration pattern. These results indicate that the PEN5α and PEN5β differ markedly in their carbohydrates composition, and that ~85% of the apparent m.w. of PEN5α is due to N-linked carbohydrates.

PEN5α Contains 80% N-Linked Keratanase-Sensitive Carbohydrates, Whereas PEN5β Contains 80% O-Linked Keratanase-Sensitive Carbohydrates The extensive N-linked glycosylation of PEN5α suggested that it might be a member of one of the two major groups of glycoproteins characterized by such high carbohydrate content (50 to 90%), i.e: proteoglycans and mucin-type glycoproteins. Chondroitinase ABC, heparitinase and heparinase did not affect the migration pattern of PEN5α or PEN5β (data not shown). By contrast, incubation of PEN5 molecules with keratanase I reduced the apparent m.w. of PEN5α from 210–245 kDa to 35–40 kDa (FIG. 6, lane 2; c1). It is likely that the difference between the PNgase F-digested (35–40 kDa) c1 core protein (FIG. 6, lane 6) and the keratanase-digested (25–30 kDa) c2 core protein (FIG. 6, lane 4), is the consequence of a more complete deglycosylation of the PEN5α glycoprotein. Whereas keratanase treatment only slightly reduced the polydispersity of PEN5β, the combination of O-glycanase and keratanase I treatment reduced the apparent m.w. of PEN5α from 120–170 kDa to 25–30 kDa (FIG. 6, lane 4). Taken together, these results indicate that, by weight, PEN5α contains ~80% N-linked keratanase I-sensitive carbohydrates, whereas PEN5β contains ~80% O-linked keratanase I-sensitive carbohydrates. In addition, treatment with neuraminidase induced a slight reduction in the polydispersity, as well as a shift in the apparent m.w. of both PEN5α and β, indicating that sialic acid residues are also present on both glycoproteins (FIG. 6, lane 5). Treatment of PEN5 glycoproteins with a combination of PNGase F and neuraminidase (FIG. 6, lane 7), resulted in the same effect that PNGase F alone, confirming the presence of terminal sialic acid residues on N-linked carbohydrates present on PEN5α. The c1 and c2 deglycosylated forms of PEN5α and β proteins were not immunoprecipitable by the 5H10 mAb (data not shown), indicating that the epitope recognized by the anti-PEN5 mAb requires the keratanase I-sensitive carbohydrate chains.

Example 4
Reactivity of anti-PEN5 mAb with keratan sulfate glycosaminoglycans In order to test whether the anti-PEN5 mAb was directed against keratan sulfate carbohydrates, we next examined the effect of exogenous keratan sulfate carbohydrates on the binding of PEN5 mAb to NK cells. Radioiodinated 5H10 (anti-PEN5) mAb was combined with various concentrations of bovine cornea keratan sulfate proteoglycan (BC), and the mixture was then incubated with NK cells.

Figure 7A:
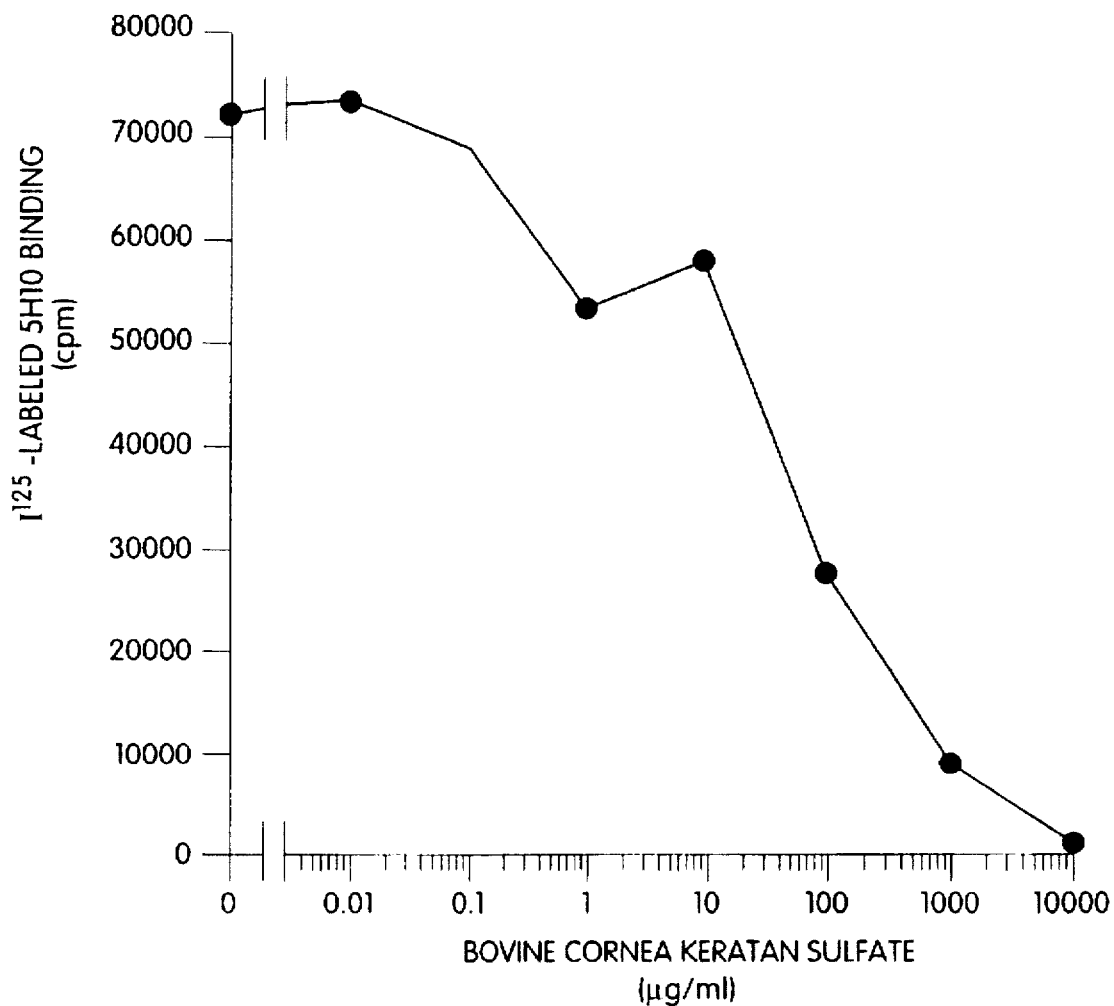
FIGS. 7A through 7C illustrate the reactivity of anti-PEN5 mAb with keratan sulfate glycosaminoglycans.

Briefly, $I^{125}$-labeled 5H10 mAb ($1 \times 10^6$ cpm/sample) was preincubated for 20 min at 4° C. in PBS in the presence of the concentrations of bovine cornea keratan sulfate (BC) indicated in FIG. 7A. The mixture was then added to NK cells for another 20 min incubation at 4° C., prior to three washes in PBS-1%BSA. Samples were counted in a τ-counter, and results were expressed as mean cpm of duplicate samples (SD<10%)). When used in incubation with NK cells or anti-PEN5 mAb, the following carbohydrates used at 10 mg/ml were without any effect on 5H10 binding to NK cell surface: chondroitin sulfate B, heparin, heparan sulfate, dextran sulfate, GlcNAC, mannose 6-phosphate, lactose, galactose-6-phosphate, fucose, glucose 6-phosphate, glucose and galactose.

As shown in FIG. 7A, the binding of radiolabeled 5H10 mAb to NK cells was inhibited in a dose-dependent manner in the presence of BC proteoglycan. Preincubation of NK cells with the same concentrations of BC proteoglycan did not affect the binding of 5H10 mAb (data not shown), indicating that the anti-PEN5 mAb reacted with carbohydrate determinants present on keratan sulfate glycosaminoglycans. Incubation of anti-PEN5 mAb with simple sugars or other glycosaminoglycans was without any effect (see Brief Description of FIG. 7A).

Figure 7B:
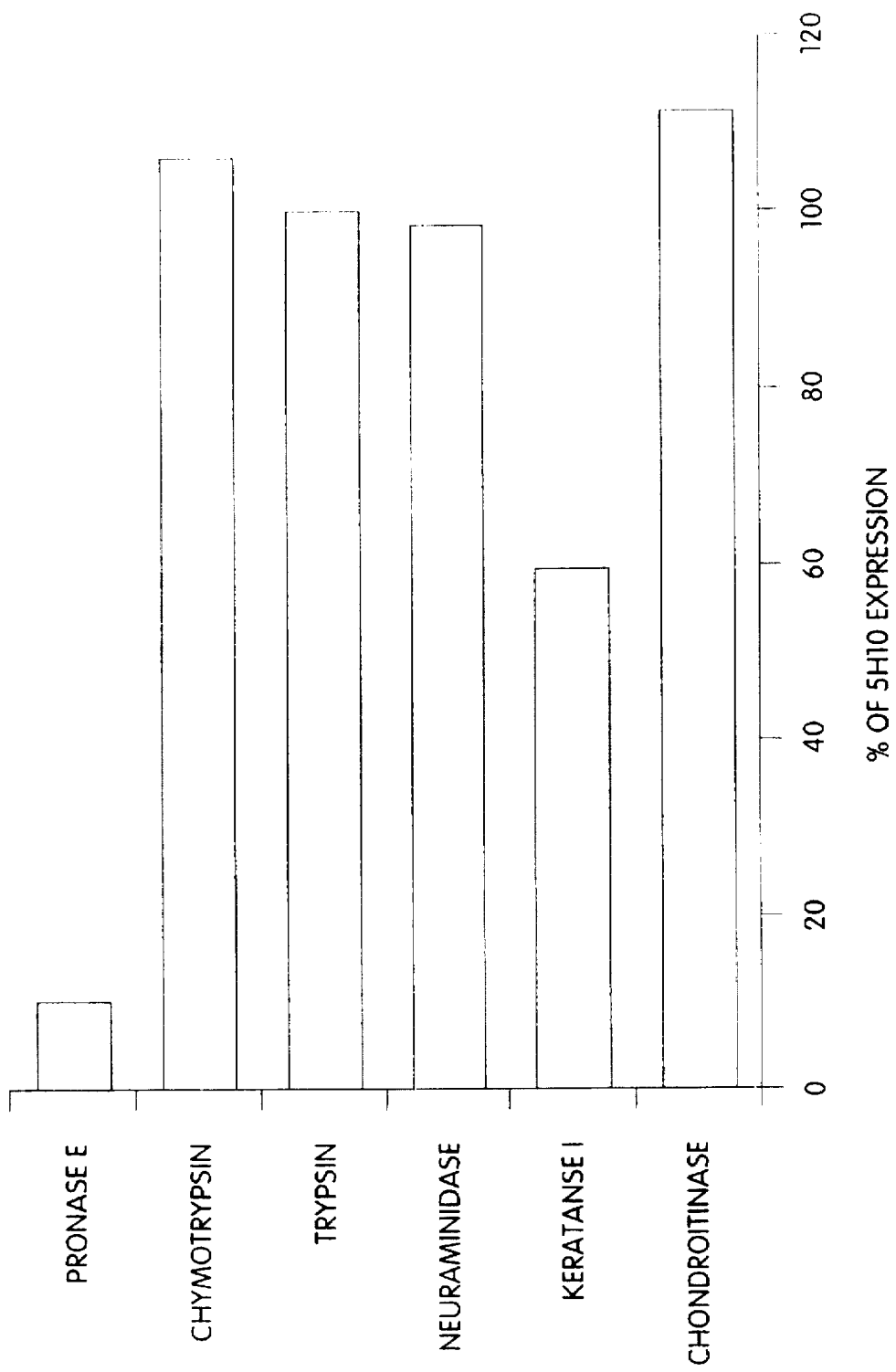

Furthermore, treatment of NK cells with keratanase I induced a 58.5%±8.4 (n=4) decrease in the reactivity of 5H10 mAb with NK cells (FIG. 7B). In FIG. 7B, peripheral blood NK cells were incubated in PBS-1%BSA for 3 hr or 45 min at 37° C. with glycosidases (0.025 U/ml) or proteases (5 mg/ml) respectively. Cell surface expression of PEN5 epitope was then analyzed by flow cytometry using 5H10 mAb. Percent modulation was calculated as the ratio of the total linear mean fluorescence intensity of the treated cells over that of untreated control cells. As illustrated in FIG. 7B, parallel treatment of NK cells with chondroitinase ABC or neuraminidase did not have any effect on 5H10 reactivity. Interestingly, the 5H10 epitope was totally insensitive to trypsin and chymotrypsin but was removed by proteinase E treatment.

Finally, an ELISA was used to compare the binding of 5H10(anti-PEN5) and 5D4 (anti-keratan sulfate) to the keratan sulfate proteoglycans expressed in various tissues. The antigenicity of 5H10 mAb for aggrecan proteoglycans was analyzed by ELISA as described in *Materials and Methods*. The anti-keratan sulfate mAb 5D4 was used as a positive control. Chondroitinase ABC was used at 0.04 U/ml, keratanase I was used at 0.05 U/ml and keratanase II was used at 0.004 U/ml, for 1 hr at 37° C.

Figure 7C:
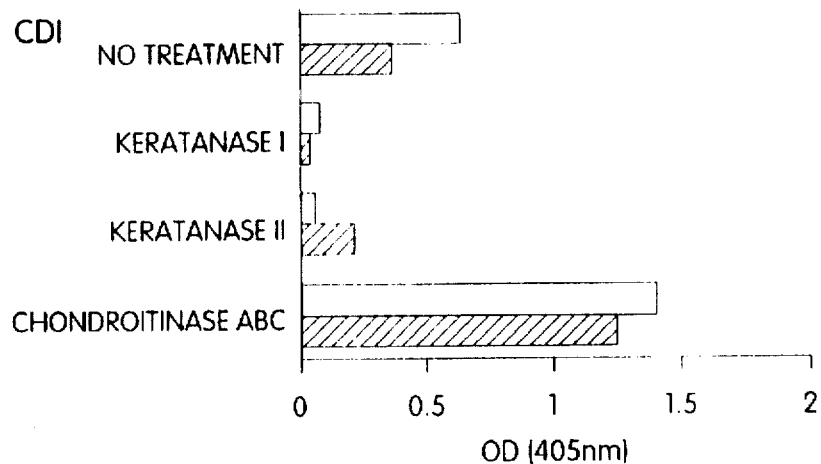
Figure 7D:
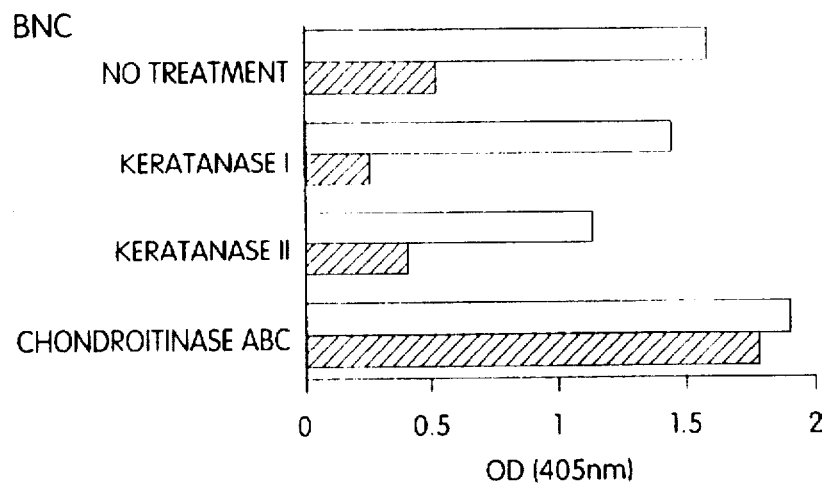
Figure 7E:
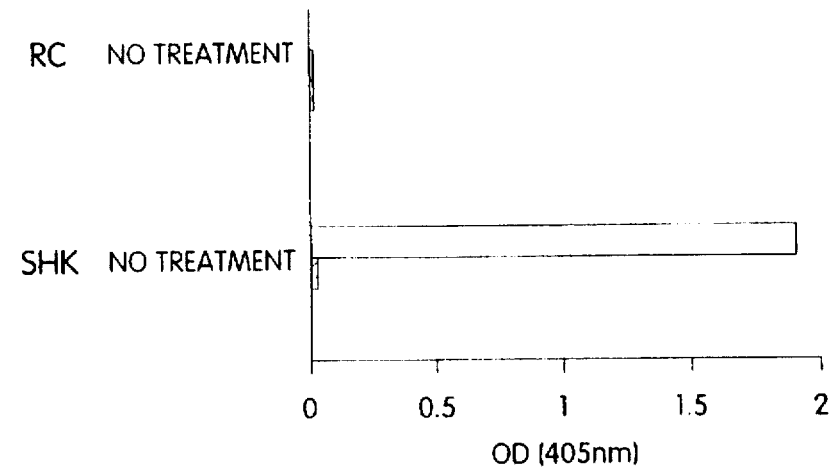

As illustrated in FIG. 7C (upper panel), the 5H10 mAb (cross-hatched) recognized aggrecan-type proteoglycans derived from embryonic chick cartilage (CD1, upper panel) and from bovine nasal cartilage (BNC, middle panel). As a positive control, the anti-keratan sulfate mAb 5D4 (open bars) also reacted with untreated CD1 and BNC, whereas its reactivity with keratanase-treated samples was reduced. Treatment of CD1 and BWC with either keratanase I or II, reduced 5H10 reactivity. Treatment of CD1 and BNC with chondroitinase ABC is known to increase the expression of keratan sulfate epitopes. Consequently, digestion of CD1 and BNC with chondroitinase ABC increased the binding of both 5H10 and 5D4. As a negative control, neither mAb recognized the Swarm rat chondrosarcoma aggrecan (RC), which does not contain keratan sulfate (FIG. 7C, lower panel). Although 5D4 also reacted with the keratan sulfate proteoglycan isolated from shark cranial cartilage (SHK), 5H10 did not. These results indicate that the 5H10epitope is present in some, but not all, keratan sulfate chains. Although 5H10 can clearly recognize an epitope expressed on certain keratan sulfate chains, the epitope expressed on the PEN5 molecule on NK cells is not simply a keratan sulfate chain since flow cytometric analysis using 6 distinct anti-keratan sulfate mAbs 1B4, 2D3, 3D2, 4D1, 8C2, and 5D4 did not detect binding to NK cells (data not shown).

Taken together, these results indicate that 5H10 recognizes an epitope that, although present on keratan sulfate carbohydrates, is distinct from the standard sulfated polylactosamine repeat sequence, Galb1-4(sulfated)GlcNAc.

Figure 8A:
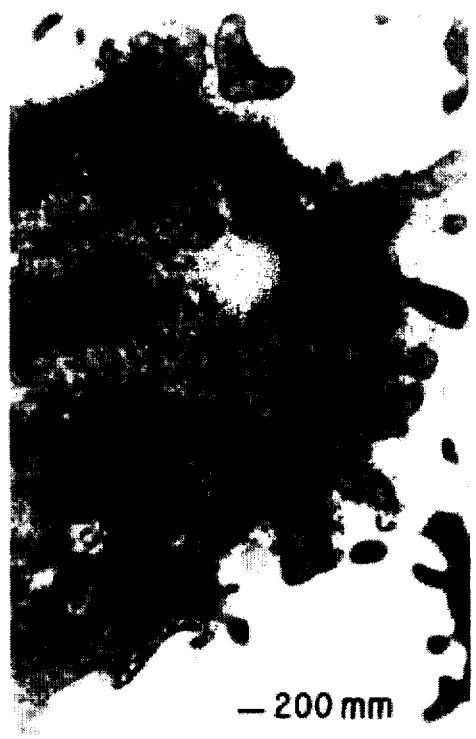
FIGS. 8A through 8C illustrate the results of immunogold staining of the PEN5 epitope on NK cells. Peripheral blood NK cells were stained with anti-PEN5 mAb followed by gold-labeled anti-mouse IgM antibodies, and glutaraldehyde-fixed cells were then analyzed by transmission electron microscopy. Magnification: ×48500. 0.972 cm=200 nm. The three photomicrographs 8A–8C represent different views of the same stained cell.
Figure 8B:
Figure 8C:
Figure 10A:
Figure 10B:
Figure 10C:
Figure 10D:
Figure 10E:
Figure 10F:

Example 5
PEN5 glycoproteins are expressed at the NK cell surface as extended rod-like structures Transmission electron microscopy was performed on NK cells stained by indirect immunofluorescence using the 5H10 mAb and a gold-labeled anti-IgM developing reagent. Ultrathin sections of NK cells showed extensive labeling at the cell surface (see. FIG. 8A–8C). Labeling was generally continuous around the entire cell profile, although in some cell preparations, there was relatively more labeling over microvilli. More striking was the distance between the plasma membrane and the gold label, which averaged 43.4 ±12.8 nm (n=50). This result suggests that, like other cell surface mucins, the membrane-bound glycoproteins carrying the PEN5 epitope are extended thread-like proteins.

Taken together, our results indicate that the PEN5 epitope is in part a carbohydrate determinant that can be expressed on keratan sulfate chains. First, keratan sulfate glycosaminoglycans selectively compete with PEN5 molecules for binding to the 5H10 (anti-PEN5) mAb. Second, treatment of NK cells with keratanase I down-regulates the cell surface expression of the PEN5 epitope. Third, the 5H10 mAb recognizes two distinct aggrecan-type keratan sulfate proteoglycans. Keratan sulfates are glycosaminoglycans consisting of repeated Galb1-4(sulfated)GlcNac disaccharides. Within this constraint, differential branching of the disaccharide subunits, differential sulfation of GlCNAc, and differential fucoslyation and/or sialylation of the Galb1-4 (sulfacted)GlcNAc can lead to heterogeneity in individual keratan sulfate chains. The lack of reactivity of anti-PEN5 mAb with the keratan-sulfate proteoglycan SHK isolated from shark cranial cartilage suggests that the standard lactosaminoglycan repeat sequence is not the epitope recognized by 5H10. Rather, our data indicate that 5H10recognizes an unusual sulfated polylactosamine epitope present on some but not all keratan sulfate glycosaminoglycans.

Example 6
Identification of Tissue-Infiltrating Natural Killer Cells Expressing the Mucinlike Glycoprotein PEN51
Materials and Methods
The following methods and materials apply to Examples 6A through 6D.
Source of Tissues
Histologically normal fetal (20 week gestation) and adult human tissues were obtained from surgical and autopsy specimens. Frozen tissues embedded in OCT compound (Baxter Corp., McGaw Park, Ill.) were stored at −70° C. until needed. All tissues were used as frozen tissue sections and were adequately preserved historically. The panel of normal tissues that were screened included adrenal, brain, breast, cervix, colon, esophagus, heart, kidney, liver, lung, lymph node, ovary, peripheral nerve, pancreas, skeletal muscle, skin, small intestine, spleen, stomach, testis, thyroid, tonsils, thymus, and uterus.
Reagents
Anti-5H10 was used at a dilution of 1:400 (2.5 mg/ml) in phosphate buffered saline (PBS) containing 0.06% crystalline bovine serum albumin (BSA) and 0.1% sodium azide. Purified mouse IgM (Coulter Immunology, Hialeah, Fla.) served as the negative control. For use it was diluted to the same concentration, with the same buffer solution as the test antibody. N901, a murine monoclonal antibody of the IgG1 subclass, binds to the NKH1 antigen (CD56) expressed on NK cells. The antibody was used at a dilution of 1:664 (2.5 mg/ml) in PBS containing 0.06% crystalline bovine serum albumin (BSA) and 0.1% sodium azide. Biotinylated affinity purified goat anti-mouse IgM (m chain specific) and horse anti-mouse IgG (heavy+light chain specific) antibodies (Vector Laboratories, Inc,. Burlingame, Calif.) were utilized as secondary antibodies at a dilution of 1:150 in PBS containing 2% human AB$^+$ serum and 0.1% sodium azide. Avidin-biotin-peroxidase complexes (Vector) were used as the labeling reagent at a dilution of 1:1:80 in PBS.
Immunohistochemistry
Immunohistochemical studies were performed using the avidin-biotin immunoperoxidase technique [Rice, et al., *Am. J. Path.*, 138:385, (1991)]. To assure that tissue sections adhered, slides were coated with poly-L-lysine (Sigma Chemical Co., St. Louis, Mo.) reconstituted in purified water. Frozen sections were cryostat cut (6–8 mm thick), collected onto coated slides, air dried and fixed in 2% neutral buffered paraformaldehyde at 4° C. for 20 minutes, followed by several washes with PBS. To block endogenous biotin content, and reduce cross-reactivity of the biotinylated antibody, all tissues were incubated with a solution of avidin (Vector) and 10% normal horse serum (Vector) in BSA dilution buffer, at room temperature for 15 minutes. Tissue sections were drained of avidin/horse serum buffer and incubated with the antibody at 4° C., overnight. After washing in PBS, slides were incubated for 30 minutes in 0.3% hydrogen peroxide and biotin blocking solution to quench endogenous peroxidase activity and to block remaining avidin. Sections were then washed with PBS, incubated with either biotinylated goat anti-mouse IgM or horse anti-mouse IgG antibodies for 30 minutes, washed in PBS, incubated with avidin-biotin-peroxidase complexes for 45 minutes, and then washed again with PBS. After incubating the slides for 5 minutes in Tris-Imidazole/HCL buffer, the peroxidase reaction was initiated by incubating for 5 minutes with 3,3-diaminobenzidine (DAB) (Sigma Chemical Co.) dissolved in Tris-Imidazole/HCL buffer containing 0.11% hydrogen peroxide. Tissue sections were washed in water, counterstained with Harris hematoxylin, and dehydrated through graded alcohols and xylenes. Coverslips were then mounted on slides with E-Z-Mount mounting media (Shandon Inc., Pittsburgh, Pa.).
Transmission Electron Microscopy
Peripheral blood NK cells purified as reported in Vivier, et al., *J. Immunol.*, 146:206, (1991) were first stained using 5H10 (anti-PEN5) and colloidal gold-labeled goat anti-mouse IgM (Amersham). After fixation for 1 hour in 0.1% glutaraldehyde, 2% paraformaldehyde, the stained cells were examined by transmission electron microscopy as described in Watkins, et al., *Carbohydrate Res.*, 213:185, (1991).

Example 6A
Comparative expression of PEN5$^+$ and CD56$^+$ lymphocytes infiltrating lymphoid tissues
Although CD56 is expressed on the surface of most peripheral blood NK cells, its density of expression on most NK cells is quite low. Because of this, antibodies reactive with CD56 may not be ideal reagents for the identification of tissue infiltrating NK cells. The relative inability of anti-CD56 to detect NK cells in lymphoid tissues is demonstrated in FIGS. 9 and 10, in which CD56$^+$ cells are rarely detected in lymph node, tonsil, or thymus. In contrast, antibodies reactive with PEN5 identified lymphocytes infiltrating each of these tissues. Whereas PEN5$^+$ cells were scattered throughout the lymph node, they tended to be concentrated in the parafollicular areas of the tonsil. At higher magnification, PEN5$^+$ cells were observed to be round or oval or occasionally elongated. They were generally larger than resting tissue lymphocytes, containing a relatively abundant cytoplasm. The nuclei were set eccentrically within the cells, and were slightly larger than those of resting lymphocytes. The nuclear chromatin was dense and homogeneous. Immunostaining was usually in the region of the plasma membrane, but was also seen in the cytoplasm.

Example 6B
Comparative expression of PEN5$^+$ and CD56$^+$ lymphocytes in fetal and adult tissues
Because fetal liver and fetal thymus have been implicated as sites of NK cell differentiation, we compared the expression of PEN5$^+$ and CD56$^+$ lymphocytes in each of these tissues to that of their adult counterparts. As shown in FIG. 10, CD56$^+$ cells were not easily detected in either fetal or adult thymus. In each of these tissues, scattered lymphocytes expressing low levels of CD56 could be detected at high magnification, suggesting that CD56$^+$cells are present, but difficult to detect using this histochemical method. This might result from lability of the antigen under these fixation conditions, or the low level of CD56 expression, since Sanchez, et al [*J. Exp. Med.* 178:1857 (1993)] have shown that CD56$^+$lymphocytes can be identified in these tissues using flow cytometric analysis. In contrast, PEN5$^+$ cells were easily detected, scattered throughout both adult and fetal thymus. The density of PEN5$^+$ cells was consistently greater in fetal thymus than in adult thymus. Occasional CD56$^+$ cells could be detected in adult liver, but again, the intensity of staining was very weak (FIG. 11). Scattered PEN5+ cells were easily detected in the adult liver, due to their more intense staining. Relatively more PEN5$^+$ cells were observed in fetal liver compared to adult liver. At higher magnification, PEN5 expression in liver infiltrating lymphocytes appeared, at least in part, cytoplasmic. Previous results have shown that mucin-like glycoproteins can be identified in the trans-Golgi reticulum and in cytoplasmic vesicles that eventually fuse with the plasma membrane [Watkins, et al., *Carbohydrate Res.* 213:185 (1991)]. It is possible that liver infiltrating NK cells express PEN5 primarily in these intracellular compartments.

The above results demonstrate PEN5$^+$ lymphocytes were particularly prevalent in fetal liver and fetal thymus. Recent studies suggest that NK cells and T cells arise from a common bone marrow-derived progenitor cell [Sanchez, et al., *J. Exp. Med.* 178:1857 (1993); Lanier, et al., *Immunol. Today* 13:392 (1992); Rodewald, et al., *Cell* 69:139 (1992); and Koyasu, et al., *J. Exp. Med.* 179:1957 (1994)]. Homing of these cells to the fetal liver, a major site of prenatal hematopoiesis, fosters the development of CD56$^+$ cells that resemble peripheral NK cells in both phenotype and function. Some evidence suggests that these cells can differentiate into T cells if they leave the liver and home to the thymus [Sanchez, et al., *J. Exp. Med.* 178:1857 (1993). In the absence of the thymic microenvironment, these cells can differentiate into NK cells if provided with appropriate growth factors [Sanchez, et al., *J. Exp. Med.* 178:1857 (1993); and Koyasu, et al., *J. Exp. Med.* 179:1957 (1994)]. Similarly, several studies have shown that in vitro culture of immature thymocytes in the presence of IL-2 results in the differentiation of cells which phenotypically and functionally resemble peripheral blood NK cells [Sanchez, et al., *J. Exp. Med.* 178:1857 (1993); Koyasu, et al., *J. Exp. Med.* 179:1957 (1994); Michon, et al., *J. Immun.* 140:3660 (1988); and Mingari, et al., *J. Exp. Med.* 174:21 (1991)]. Some of these studies rely on the characterization of lymphocyte clones that grow out of selected fetal and adult tissues. As clonal selection may impart a bias on any analysis of cell populations, the observation that PEN5$^+$ lymphocytes are present in fetal liver and thymus provides unbiased evidence for the differentiation of NK cells in these tissues. Although relatively few CD56$^+$ cells were identified at these sites using histochemical analysis, this result might reflect the low density of expression of this NK marker. CD56$^+$ lymphocytes have been detected in both fetal liver and fetal thymus using flow cytometric analysis [Sanchez, et al., *J. Exp. Med.* 178:1857 (1993)]. Our results suggest that PEN5 expression can be expected to be a more sensitive marker of tissue infiltrating NK cells than CD56 expression.

Example 6C

Expression of PEN5 antigen on non-lymphoid cells

Antibodies reactive with PEN5 also recognized some non-leukocytic cells. These were generally epithelial cells found in the esophagus, cervix, endometrium, trachea, bile ducts, colon and pancreas. The most dramatic example of this non-lymphoid staining was seen in the lung and colon, where anti-PEN5 strongly stained the mucous layer lining bronchial and colonic epithelial cells (FIG. 12). The specificity of this staining was confirmed by the inability of either isotype matched control antibody or anti-CD56 to stain epithelial mucosa.

Example 6D

Co-expression of PEN5 and TIA-1 in tissue infiltrating lymphocytes

Further evidence that PEN5$^+$ tissue infiltrating lymphocytes are NK cells comes from double labeling experiments using a monoclonal antibody reactive with TIA-1 (2G9, IgG1), a cytotoxic lymphocyte-restricted granule protein [Anderson, et al., *J. Immunol.* 144:574 (1990); Tian, et al., *Cell* 67:629 (1991); and Sale, et al., *Arch. Path. Lab. Med.* 116:622 (1992)]. In these experiments, PEN5$^+$ cells were identified in spleen and appendiceal lymphoid tissue using FITC-tagged anti-5H10. These same sections were also labeled using phycoerythrin-tagged anti-2G9. As shown in FIG. 13, all four PEN5$^+$ lymphocytes scattered throughout the spleen were also TIA-1$^+$. Consistent with the localization of these antigens, PEN5 staining is largely confined to the cell surface, whereas TIA-1 staining is cytoplasmic, and granular. Some PEN5cells expressed TIA-1. These cells are likely to be cytotoxic T cells which express TIA-1, but not PEN5. In the appendix, only one out of four PEN5$^+$ lymphocytes co-expressed TIA-1. This result suggests that in some tissues, PEN5 might identify less differentiated NK cells that do not possess defined cytotoxic granules. Alternatively, these results might reflect changes in the expression of TIA-1 that are related to NK cell differentiation. Table III tabulates the percentage of PEN5$^+$tissue infiltrating lymphocytes expressing TIA-1 in several tissues. As summarized below, whereas the majority of PEN5$^+$ lymphocytes co-express TIA-1 in spleen and liver, this is not the case in tonsil or appendix, where most PEN5$^+$ lymphocytes do not express TIA-1. Whether these tissue specific differences reflect different stages of NK cell differentiation, or different types of tissue infiltrating lymphocyte remains to be elucidated.

TABLE III:

Expression of TIA-1 in PEN5 ± Tissue Infiltrating Lymphocytes

| TISSUE | DONOR# | % TIA-1$^+$ |
|---|---|---|
| Spleen | 1 | 100 |
|  | 2 | 64 |
|  | 3 | 84 |
|  | 4 | 100 |
|  | 5 | 88 |
| Average: |  | 87 + 13 |
| Tonsil | 1 | 16 |
|  | 2 | 40 |
|  | 3 | 36 |
|  | 4 | 28 |
| Average: |  | 30 + 9 |
| Liver | 1 | 96 |
|  | 2 | 88 |
|  | 3 | 100 |
|  | 4 | 84 |
|  | 5 | 92 |
| Average: |  | 92 + 6 |

TABLE III:-continued

Expression of TIA-1 in PEN5 ± Tissue Infiltrating Lymphocytes

| TISSUE | DONOR# | % TIA-1+ |
|---|---|---|
| Appendix | 1 | 12 |
| | 2 | 0 |
| | 3 | 12 |
| | 4 | 4 |
| Average: | | 7 + 5 |

Dual labeling of the indicated tissues was performed as described in the Materials and Methods to Example 6, and in the brief description to FIG. 13. The percentage of PEN5+ cells that expressed TIA-1 is indicated. Tissues from 4 or 5 independent donors were evaluated, and the mean standard error is reported.

Taken together, the results provided in Examples 6A through 6D illustrate a number of important findings. We have used a monoclonal antibody reactive with a sulfated poly-N-lactosamine epitope expressed on the NK cell restricted glycoprotein PEN5 to survey the presence of tissue-infiltrating NK cells in lymphoid and non-lymphoid tissues. Whereas antibodies reactive with CD56 were unable to efficiently detect all tissue infiltrating NK cells, PEN5+ lymphocytes were readily identified in multiple tissues. Assuming that PEN5 is expressed similarly on both tissue infiltrating and circulating lymphoid cells, these results suggest that NK cells can infiltrate multiple lymphoid and non-lymphoid tissues to mediate their immune functions. In the periphery, PEN5 is selectively expressed on large granular lymphocytes possessing cytotoxic effector function. These cells express low levels of CD56, which might account for the inability of antibodies reactive with CD56 to recognize these cells in tissues. Double staining with the cytotoxic granule marker, TIA-1, supports the conclusion that PEN5+ lymphocytes infiltrating some tissues (e.g. spleen and liver) contain cytotoxic granules. Surprisingly, however, many PEN5+ cells infiltrating other tissues (e.g. tonsil and appendix) did not co-express TIA-1. This result suggests that in some tissues, PEN5 might be expressed on agranular lymphocytes.

The PEN5 epitope recognized by monoclonal antibody 5H10 is related to keratan sulfate, which is itself a member of the polylactosamine family of sugars. The two isoforms of PEN5 thus resemble a keratan sulfate proteoglycan (PEN5β) and a keratan sulfated mucin (PEN5α). Secreted mucins derivatized with keratan sulfate have been identified in the tracheal mucosa [Kim, et al., *Exp. Lung Res.* 17:533 (1991)]. It is possible that the recognition of the tracheal and gastrointestinal mucin layer by anti-5H10 results from its recognition of these keratan sulfated mucins. We have previously shown that anti-5H10 can recognize keratan sulfate-bearing proteoglycans derived from several tissues, including embryonic chick cartilage and bovine nasal aggrecan [Vivier, et al., *J. Exe. Med.* 178:2023 (1993)]. In epithelial cells, mucins are secreted to provide protection against environmental toxins [Strous, et al., *Critical Rev. in Biochem. and Molec. Biol.* 27:57 (1992)]. It is possible, by analogy, that PEN5is expressed on differentiated large granular NK cells to protect them against their own cytotoxic effector molecules. The extended, rod-like structure of PEN5 demonstrated by transmission electron microscopy could facilitate such a functional role. Cell surface mucins have also been identified as ligands for lymphocyte adhesion molecules involved in tissue homing [Lasky, et al., *Cell* 69:927 (1992)]. It is therefore possible that the expression of PEN5 on terminally differentiated NK cells allows its subsequent infiltration into the various tissues in which these cells are found.

Having described the invention, what is claimed is:

1. A monoclonal antibody which forms an immune complex with the glycoprotein PEN5.

2. An antibody according to claim 1 or an immunoreactive fragment thereof, attached to a label.

3. An antibody according to claim 2, wherein the label is a fluorescent, radioactive, or enzymatic label.

4. An antibody according to claim 1, or an immunoreactive fragment thereof, attached to a toxin.

5. An antibody according to claim 1, or an immunoreactive fragment thereof, attached to a solid support.

6. An antibody according to claim 1, which is reactive with the PEN5 glycoprotein present on the surface of a natural killer cell.

7. An antibody according to claim 1, which is unreactive with antigens present on T cells, B cells, monocytes, granulocytes, red blood cells and platelets.

8. An antibody according to claim 1, which recognizes an epitope on the PEN5 glycoprotein comprising a sulfated polylactosamine carbohydrate molecule.

9. An antibody according to claim 8, wherein the epitope is present on the surface of about 70% to 90% of functionally differentiated natural killer cells, and is not present on CD3+ T cells or CD20+ B cells.

10. An antibody according to claim 1, which is a chimeric antibody.

11. An immunoreactive fragment of an antibody according to claim 1.

12. An antibody according to claim 1, which is a mouse monoclonal antibody.

13. An antibody according to claim 1, which forms an immune complex with the same epitope as the monoclonal antibody produced by the hybridoma identified by ATCC Accession No. HB11441.

14. An antibody according to claim 1, which is produced by the hybridoma identified by ATCC Accession No. HB11441.

15. A hybridoma that produces a monoclonal antibody which forms an immune complex with the glycoprotein PEN5.

16. A hybridoma according to claim 15, which is identified by ATCC Accession No. HB11441.

17. A method for detecting the presence of natural killer cells in a biological sample, comprising the steps of:
 (a) contacting the biological sample with a monoclonal antibody, or an immunoreactive fragment or derivative thereof, which forms an immune complex with the natural killer cell surface glycoprotein PEN5 under conditions sufficient to allow the immune complex to form; and
 (b) detecting the immune complex as an indicator of the presence of natural killer cells in the biological sample.

18. A method according to claim 17, wherein the monoclonal antibody is attached to a label.

19. A method according to claim 18, wherein the monoclonal antibody is labeled with a detectable label selected from the group consisting of a radioisotope, a fluorescent label, or an enzyme.

20. A method according to claim 19, wherein said biological sample is a sample of peripheral blood or bone marrow.

21. A method according to claim 19, wherein the label is a fluorescent label selected from the group consisting of rhodamine, phycoerythrin, and fluorescein isothiocyanate.

22. The method according to claim 17, wherein the biological sample is a tissue sample.

23. The method according to claim 22, wherein the tissue sample is from lymphoid tissue.

24. The method according to claim 22, wherein the tissue sample is from non-lymphoid tissue.

25. The method according to claim 22, wherein the tissue sample is selected from the group consisting of adrenal, brain, breast, cervix, colon, esophagus, heart, kidney, liver, lung, lymph node, ovary, peripheral nerve, pancreas, skeletal muscle, skin, small intestine, spleen, stomach, testis, thyroid, tonsils, thymus, and uterus.

26. The method according to claim 22, further including the step of contacting the biological sample with a monoclonal antibody reactive with the cytotoxic lymphocyte-restricted granule protein TIA-1.

27. A method for selectively removing natural killer cells from a biological sample comprising the steps of:
  (a) contacting the biological sample with a monoclonal antibody, or immunoreactive fragment or derivative thereof, which forms an immune complex with the natural killer cell surface glycoprotein PEN5 under conditions sufficient to allow the immune complex to form; and
  (b) removing cells comprising the immune complex from the biological sample.

28. A method according to claim 27, wherein the biological sample is peripheral blood or bone marrow aspirate.

29. A method according to claim 28, wherein the sample is contacted with the antibody or immunoreactive fragment thereof in the presence of complement.

30. A method according to claim 28, wherein the monoclonal antibody is conjugated to a toxin.

31. A kit for detecting or removing natural killer cells from a biological sample comprising a monoclonal antibody, or immunoreactive fragment or derivative thereof, which forms an immune complex with the natural killer cell-surface protein PEN5.

32. A kit according to claim 31, wherein the monoclonal antibody binds the same epitope as the antibody secreted by the hybridoma.

33. A kit according to claim 32, wherein the monoclonal antibody is attached to a label selected from the group consisting of rhodamine, fluorescein isothiocyanate, phycoerythrin, and biotin.

34. A kit according to claim 33, further comprising an antibody that recognizes a T cell surface antigen, CD3, and an antibody that recognizes a B cell surface antigen, CD20.

35. A kit according to claim 31, further comprising a monoclonal antibody reactive with the cytotoxic lymphocyte-restricted granule protein TIA-1.

* * * * *